United States Patent
Liu et al.

(10) Patent No.: US 9,200,045 B2
(45) Date of Patent: Dec. 1, 2015

(54) SMALL MOLECULE-DEPENDENT INTEINS AND USES THEREOF

(75) Inventors: David R. Liu, Lexington, MA (US); Sun H. Peck, Junction City, KS (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/004,280

(22) PCT Filed: Mar. 9, 2012

(86) PCT No.: PCT/US2012/028435
§ 371 (c)(1),
(2), (4) Date: Nov. 18, 2013

(87) PCT Pub. No.: WO2012/125445
PCT Pub. Date: Sep. 20, 2012

(65) Prior Publication Data
US 2014/0065711 A1    Mar. 6, 2014

Related U.S. Application Data

(60) Provisional application No. 61/452,020, filed on Mar. 11, 2011.

(51) Int. Cl.
*C07K 14/47* (2006.01)
*C07K 14/35* (2006.01)
*C12N 9/52* (2006.01)

(52) U.S. Cl.
CPC ............... *C07K 14/47* (2013.01); *C07K 14/35* (2013.01); *C12N 9/52* (2013.01); *C07K 2319/33* (2013.01); *C07K 2319/50* (2013.01); *C07K 2319/60* (2013.01); *C07K 2319/92* (2013.01)

(58) Field of Classification Search
USPC ........................................................ 530/350
See application file for complete search history.

(56) References Cited

U.S. PATENT DOCUMENTS

| 7,192,739 B2 | 3/2007 | Liu et al. |
| 7,541,450 B2 | 6/2009 | Liu et al. |

FOREIGN PATENT DOCUMENTS

WO    WO 2005/098043 A2    10/2005

OTHER PUBLICATIONS

Elleuche et al. (Appl Microbiol Biotechnol (2010) 87;479-489).*
International Search Report and Written Opinion for PCT/US2012/028435, mailed Sep. 19, 2012.
International Preliminary Report on Patentability for PCT/US2012/028435, mailed Sep. 26, 2013.
GENBANK Submission: NIH/NCBI, Accession No. NP_000116, Hoteit et al.; Feb. 26, 2014.
GENBANK Submission: NIH/NCBI, Accession No. NP_001116212, Hoteit et al.; Feb. 18, 2014.
GENBANK Submission: NIH/NCBI, Accession No. NP_001116213, Hoteit et al.; Feb. 18, 2014.
GENBANK Submission: NIH/NCBI, Accession No. NP_001116214, Hoteit et al.; Feb. 18, 2014.
Acar et al., A general mechanism for network-dosage compensation in gene circuits. Science. Sep. 24, 2010;329(5999):1656-60. doi: 10.1126/science.1190544.
Banaszynski et al., A rapid, reversible, and tunable method to regulate protein function in living cells using synthetic small molecules. Cell. Sep. 8 2006;126(5):995-1004.
Banaszynski et al., Conditional control of protein function. Chem Biol. Jan. 2006;13(1):11-21. Review.
Bayle et al., Rapamycin analogs with differential binding specificity permit orthogonal control of protein activity. Chem Biol. Jan. 2006;13(1):99-107.
Becker et al., Fusion of adenovirus E1A to the glucocorticoid receptor by high-resolution deletion cloning creates a hormonally inducible viral transactivator. Mol Cell Biol. Sep. 1989;9(9):3878-87.
Boehmelt et al., Hormone-regulated v-rel estrogen receptor fusion protein: reversible induction of cell transformation and cellular gene expression. EMBO J. Dec. 1992;11(12):4641-52.
Braselmann et al., A selective transcriptional induction system for mammalian cells based on Gal4-estrogen receptor fusion proteins. Proc Natl Acad Sci U S A. Mar. 1, 1993;90(5):1657-61.
Braselmann et al., Identification of Fos target genes by the use of selective induction systems. J Cell Sci Suppl. 1992;16:97-109. Review.

(Continued)

*Primary Examiner* — James H Alstrum Acevedo
*Assistant Examiner* — Tara Martinez
(74) *Attorney, Agent, or Firm* — Wolf, Greenfield & Sacks, P.C.

(57) ABSTRACT

Elucidating the function of proteins in mammalian cells is particularly challenging due to the inherent complexity of these systems. Methods to study protein function in living cells ideally perturb the activity of only the protein of interest but otherwise maintain the natural state of the host cell or organism. Ligand-dependent inteins offer single-protein specificity and other desirable features as an approach to control protein function in cells post-translationally. Some aspects of this invention provide second-generation ligand-dependent inteins that splice to substantially higher yields and with faster kinetics in the presence of the cell-permeable small molecule 4-HT, especially at 37° C., while exhibiting comparable or improved low levels of background splicing in the absence of 4-HT, as compared to the parental inteins. These improvements were observed in four protein contexts tested in mammalian cells at 37° C., as well as in yeast cells assayed at 30° C. or 37° C. The newly evolved inteins described herein are therefore promising tools as conditional modulators of protein structure and function in yeast and mammalian cells.

12 Claims, 8 Drawing Sheets

(56) References Cited

OTHER PUBLICATIONS

Buskirk et al., Creating small-molecule-dependent switches to modulate biological functions. Chem Biol. Feb. 2005;12(2):151-61. Review.

Buskirk et al., Directed evolution of ligand dependence: small-molecule-activated protein splicing. Proc Natl Acad Sci U S A. Jul. 20, 2004;101(29):10505-10. Epub Jul. 9, 2004.

Christopherson et al., Ecdysteroid-dependent regulation of genes in mammalian cells by a Drosophila ecdysone receptor and chimeric transactivators. Proc Natl Acad Sci U S A. Jul. 15, 1992;89(14):6314-8.

Danielian et al., Modification of gene activity in mouse embryos in utero by a tamoxifen-inducible form of Cre recombinase. Curr Biol. Dec. 3, 1998;8(24):1323-6.

Eilers et al., Chimaeras of myc oncoprotein and steroid receptors cause hormone-dependent transformation of cells. Nature. Jul. 6, 1989;340(6228):66-8.

Fankhauser et al., The hormone binding domain of the mineralocorticoid receptor can regulate heterologous activities in cis. Biochem Biophys Res Commun. Apr. 15, 1994;200(1):195-201.

Feil et al., Ligand-activated site-specific recombination in mice. Proc Natl Acad Sci U S A. Oct. 1, 1996;93(20):10887-90.

Fire et al., Potent and specific genetic interference by double-stranded RNA in Caenorhabditis elegans. Nature. Feb. 19, 1998;391(6669):806-11.

Godowski et al., Signal transduction and transcriptional regulation by glucocorticoid receptor-LexA fusion proteins. Science. Aug. 12, 1988;241(4867):812-6.

Gossen et al, Tight control of gene expression in mammalian cells by tetracycline-responsive promoters. Proc Natl Acad Sci U S A. Jun. 15, 1992;89(12):5547-51.

Hartley et al., Mechanisms that specify promoter nucleosome location and identity. Cell. May 1, 2009;137(3):445-58. doi: 10.1016/j.cell.2009.02.043.

Kellendonk et al., Regulation of Cre recombinase activity by the synthetic steroid RU 486. Nucleic Acids Res. Apr. 15, 1996;24(8):1404-11.

Koebernick et al., Gli-type zinc finger proteins as bipotential transducers of Hedgehog signaling. Differentiation. May 2002;70(2-3):69-76.

Lee et al., A chimeric thyroid hormone receptor constitutively bound to DNA requires retinoid X receptor for hormone-dependent transcriptional activation in yeast. Mol Endocrinol. Sep. 1994;8(9):1245-52.

Lew et al., An in vivo screening system against protein splicing useful for the isolation of non-splicing mutants or inhibitors of the RecA intein of *Mycobacterium tuberculosis*. Gene. Jan. 9, 2002;282(1-2):169-77.

Mootz et al., Activation of an autoregulated protein kinase by conditional protein splicing. Angew Chem Int Ed Engl. Oct. 4, 2004;43(39):5189-92.

Mootz et al., Conditional protein splicing: a new tool to control protein structure and function in vitro and in vivo. J Am Chem Soc. Sep. 3, 2003;125(35):10561-9.

Mootz et al., Protein splicing triggered by a small molecule. J Am Chem Soc. Aug. 7, 2002;124(31):9044-5.

No et al., Ecdysone-inducible gene expression in mammalian cells and transgenic mice. Proc Natl Acad Sci U S A. Apr. 16, 1996;93(8):3346-51.

Paulus, Protein splicing and related forms of protein autoprocessing. Annu Rev Biochem. 2000;69:447-96.

Peck et al., Directed evolution of a small-molecule-triggered intein with improved splicing properties in mammalian cells. Chem Biol. May 27, 2011;18(5):619-30. doi:10.1016/j.chembiol.2011.02.014.

Picard, Posttranslational regulation of proteins by fusions to steroid-binding domains. Methods Enzymol. 2000;327:385-401.

Pratt et al., Small-molecule-mediated rescue of protein function by an inducible proteolytic shunt. Proc Natl Acad Sci U S A. Jul. 3, 2007;104(27):11209-14. Epub Jun. 11, 2007.

Sauer et al., Site-specific DNA recombination in mammalian cells by the Cre recombinase of bacteriophage P1. Proc Natl Acad Sci U S A. Jul. 1988;85(14):5166-70.

Schneekloth et al.,Chemical genetic control of protein levels: selective in vivo targeted degradation. J Am Chem Soc. Mar. 31, 2004;126(12):3748-54.

Schwartz et al., Post-translational enzyme activation in an animal via optimized conditional protein splicing. Nat Chem Biol. Jan. 2007;3(1):50-4. Epub Nov. 26, 2006.

Shi et al., Development of a tandem protein trans-splicing system based on native and engineered split inteins. J Am Chem Soc. May 4, 2005;127(17):6198-206.

Shogren-Knaak et al., Recent advances in chemical approaches to the study of biological systems. Annu Rev Cell Dev Biol. 2001;17:405-33.

Smith, et al., Expression of a dominant negative retinoic acid receptor g in Xenopus embryos leads to partial resistance to retinoic acid. Roux's Arch. Dev. Biol. 1994;203:254-265.

Stankunas et al., Conditional protein alleles using knockin mice and a chemical inducer of dimerization. Mol Cell. Dec. 2003;12(6):1615-24.

Wang et al., Inducible protein knockout reveals temporal requirement of CaMKII reactivation for memory consolidation in the brain. Proc Natl Acad Sci U S A. Apr. 1, 2003;100(7):4287-92. Epub Mar. 19, 2003.

Wong et al., Transcriptional compensation for gene loss plays a minor role in maintaining genetic robustness in Saccharomyces cerevisiae. Genetics. Oct. 2005;171(2):829-33. Epub Jul. 5, 2005.

Xu et al., In vitro protein splicing of purified precursor and the identification of a branched intermediate. Cell. Dec. 31, 1993;75(7):1371-7.

Yuen et al., Control of transcription factor activity and osteoblast differentiation in mammalian cells using an evolved small-molecule-dependent intein. J Am Chem Soc. Jul. 12, 2006;128(27):8939-46.

Zhang et al., Inducible site-directed recombination in mouse embryonic stem cells. Nucleic Acids Res. Feb. 15, 1996;24(4):543-8.

Zhao et al., In vitro 'sexual' evolution through the PCR-based staggered extension process (StEP). Nat Protoc. 2006;1(4):1865-71.

\* cited by examiner

SMALL MOLECULE-DEPENDENT INTEINS AND USES THEREOF

RELATED APPLICATION

This application is a national stage filing under 35 U.S.C. §371 of international PCT application, PCT/US2012/028435, filed Mar. 9, 2012, which claims priority under 35 U.S.C. §119(e) to U.S. provisional patent application, U.S. Ser. No. 61/452,020, filed Mar. 11, 2011, entitled "Small Molecule-Dependent Inteins and Uses Thereof," the entire contents of each of which are incorporated herein by reference.

GOVERNMENT SUPPORT

This invention was made with U.S. Government support under grant R01 GM065400, awarded by the National Institutes of Health (NIH), and grant HR0011-08-1-0085, awarded by the Defense Advanced Research Projects Agency (DARPA). The U.S. government has certain rights in this invention.

BACKGROUND OF THE INVENTION

Methods to control protein structure and function inside living cells have proven to be valuable tools to elucidate the roles of proteins in their native biological contexts (Schreiber, 2003; Buskirk and Liu, 2005; Banaszynski and Wandless, 2006). Traditional genetic methods that have been widely used to control protein function by altering expression levels in mammalian cells include knock-out and knock-in systems such as those mediated by Cre-Lox recombination (Sauer et al., 1988) and the use of transcriptional regulators such as the tetracycline-responsive tet-on/tet-off systems (Gossen et al., 1992). These methods are highly specific to the protein of interest and can be applied to many proteins, but typically require days to reach steady-state protein levels in mammalian cells, are irreversible in the case of recombination-based methods, and are vulnerable to transcriptional compensation (Shogren-Knaak et al., 2001; Marschang et al., 2004; Wong and Roth, 2005; Acar et al., 2010). Other methods such as RNA interference (Fire et al., 1998), chemical genetics (Kino et al., 1987), small-molecule regulated protein stability or degradation (Stankunas et al., 2003; Schneekloth et al., 2004; Banaszynski et al., 2006), and small molecule induced proteolytic shunts (Pratt et al., 2007) have also been used effectively by many researchers and offer more rapid control over protein levels than strategies that exert control before transcription, but can require the discovery of small molecule modulators of protein function, necessitate the involvement of other cellular machinery that may not be present in the cells of interest, or are prone to off-target effects.

Protein-splicing elements, termed inteins, can mediate profound changes in the structure and function of proteins. Inteins are analogous to the introns found in polynucleotides. During intein-mediated protein splicing, inteins catalyze both their own excision from within a polypeptide chain and the ligation of the flanking external sequences (exteins), resulting in the formation of the mature protein from the exteins, and the free intein. No natural inteins, however, have been shown to be regulated by small molecules. Extein function is typically disrupted by the presence of an intein but restored after protein splicing. Many inteins can splice in foreign extein environments. Therefore, inteins are powerful starting points for the creation of artificial molecular switches.

Ligand-dependent inteins have been engineered (see, e.g., PCT application WO 2005/098043). Since inteins function in a variety of extein environment, ligand-dependent inteins are universally applicable to regulate the activity of a variety of target proteins in mammalian cells in a ligand-dependent manner without disturbing transcriptional or translational pathways. However, conventional ligand-dependent inteins were developed for use at room temperature and exhibit poor splicing efficiency or high background splicing in the absence of ligand when incubated at higher temperatures. These characteristics limit the application of ligand-dependent inteins in mammalian cells.

SUMMARY OF THE INVENTION

Small-molecule-dependent inteins enable protein structure and function to be controlled post-translationally in living cells. Previously, two inteins were evolved (2-4 and 3-2) that splice efficiently in the presence, but not the absence, of the cell-permeable small molecule 4-hydroxytamoxifen (4-HT) in a variety of extein contexts in *Saccharomyces cerevisiae*, as described in detail in International PCT Patent Application Serial Number PCT/US2005/010805, filed Mar. 30, 2005; U.S. Pat. No. 7,192,739, issued Mar. 20, 2007; and U.S. Pat. No. 7,541,450, issued Jun. 2, 2009; the entire contents of each of which are incorporated by reference herein. In mammalian cells, however, the 2-4 and 3-2 inteins exhibited significantly lower splicing efficiencies and slower splicing in the presence of 4-HT, as well as higher background splicing in the absence of 4-HT, than in yeast cells. These inteins are described in detail in International PCT Patent Application Serial Number PCT/US2005/010805, filed Mar. 30, 2005; U.S. Pat. No. 7,192,739, issued Mar. 20, 2007; and U.S. Pat. No. 7,541,450, issued Jun. 2, 2009; the entire contents of each of which are incorporated by reference herein.

This invention relates to the development of improved intein variants that can splice efficiently, rapidly, and/or in a ligand-dependent manner at about 37° C., for example, in cells of higher eukaryotes (e.g., mammalian cells). Results of new directed evolution efforts to improve the splicing characteristics of 4-HT dependent inteins for use at about 37° C. and in mammalian cells are described herein. The resulting second-generation inteins in yeast cells exhibit substantially improved splicing activity and speed with no significant increase in background splicing at both 30° C. and 37° C. These second-generation inteins also splice with much greater speed and efficiency in mammalian cells, for example, in human cells, at 37° C. in four different extein contexts compared with the parental inteins. These new ligand-dependent inteins represent more effective and broadly applicable tools for the small-molecule triggered, post-translational modulation of protein activities in living systems including mammalian cells.

In one aspect, this invention provides ligand-dependent inteins and intein domains that are optimized for applications in cells, tissues, and organisms that require incubation at temperatures in the range of about 30° C. to about 42° C., for example, at about 30° C., at about 35° C., at about 37° C., at about 37.5° C., at about 38° C., at about 38.5° C., at about 39° C., at about 39.5° C., or at about 40° C. In one aspect, this invention provides ligand-dependent inteins and intein domains that are optimized for applications in mammalian cells, tissues, and organisms, for example, in mouse or human cells, tissues, and organisms. In one aspect, this invention provides ligand-dependent inteins and intein domains that were evolved from the 2-4 and 3-2 inteins through several additional rounds of mutation, recombination, and screening in *S. cerevisiae* at both 30° C. and 37° C. The resulting second-generation evolved inteins described herein exhibit substantially improved (~2- to 5-fold higher) splicing yields in yeast compared to the parental 2-4 and 3-2 inteins and significantly faster splicing kinetics. The improved properties of these evolved inteins carried over to mammalian cells, in which the newly evolved inteins spliced with substantially greater (~2- to 8-fold) efficiency in the presence of 4-HT while maintaining background splicing levels in the absence of 4-HT that are comparable to or better than the levels observed with the 2-4 or 3-2 inteins. The second-generation evolved inteins augment the promise of ligand-dependent protein splicing as an effective and broadly applicable approach to probing protein function in mammalian cells.

In one aspect, this invention provides methods for the use of ligand-dependent inteins. In some embodiments, methods for the generation of a hybrid protein comprising a ligand-dependent intein provided herein embedded into the amino acid sequence of a target protein are provided. In some embodiments, methods for the regulation of target protein activity via ligand-dependent inteins provided herein are provided.

Other advantages, features, and uses of the invention will be apparent from the detailed description of certain non-limiting embodiments, the drawings, which are schematic and not intended to be drawn to scale, and the claims.

DEFINITIONS

Figure 1:
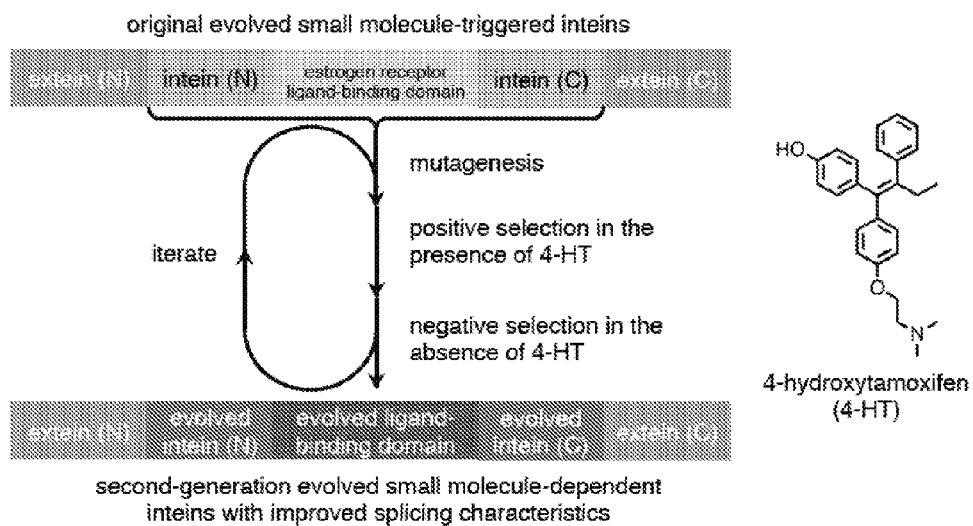
FIG. 1. Intein evolution approach. (A) Overview of the directed evolution strategy used to isolate improved small molecule-dependent inteins. (B) Each round of evolution consisted of mutagenesis followed by at least two positive FACS screens in the presence of 1 μM 4-HT and one negative FACS screen in the absence of 4-HT. One set of FACS data from the Round 1 positive and negative screens is shown. (C) Two intein evolution efforts were performed in parallel at 30° C. and 37° C., comprising 20 total screening steps.
Figure 1:
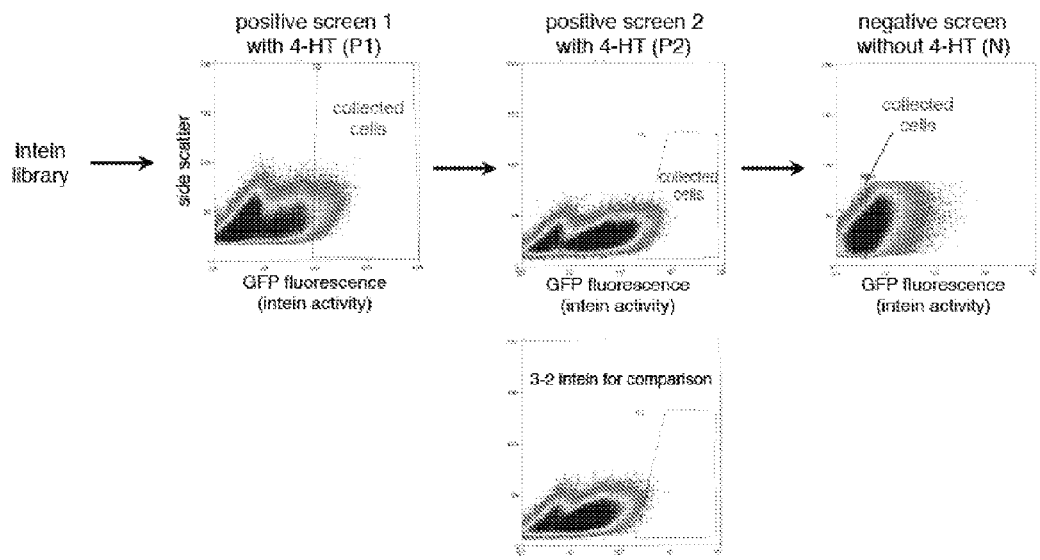
Figure 1:
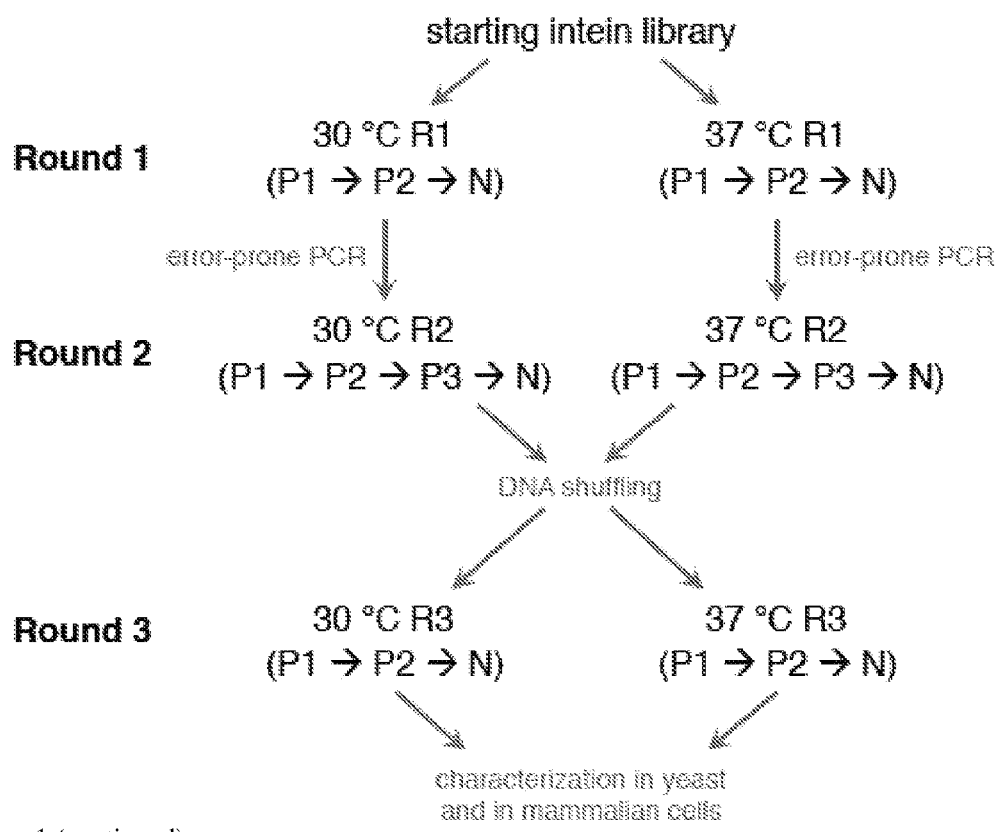

As used herein and in the claims, the singular forms "a," "an," and "the" include the singular and the plural reference unless the context clearly indicates otherwise. Thus, for example, a reference to "an agent" includes a single agent and a plurality of such agents.

The term "effective amount," as used herein, refers to an amount of a biologically active agent that is sufficient to elicit a desired biological response. For example, in some embodiments, an effective amount of 4-HT may refer to the amount of 4-HT that induces self-excision of a 4-HT-dependent intein from a hybrid protein. As will be appreciated by the skilled artisan, the effective amount of a small molecule (e.g., 4-HT), a hybrid protein, or a polynucleotide, vary depending on various factors as, for example, on the desired biological response, the cells or tissues being targeted, the agent being used, and the nature of the hybrid protein.

The term "extein," as used herein, refers to an intein-flanking polypeptide sequence that is ligated to another extein during the process of protein splicing to form a mature, spliced protein. Typically, an intein is flanked by two extein sequences that are ligated together when the intein catalyzes its own excision. Exteins, accordingly, are the protein analog to exons found in mRNA. For example, a polypeptide comprising an intein may exhibit the structure extein(N)-intein-extein(C). After excision of the intein and splicing of the two exteins, the resulting structures are extein(N)-extein(C) and a free intein.

The term "hybrid protein," as used herein, refers to a protein that comprises the amino acid sequence of a target protein and, embedded in that amino acid sequence, a ligand-dependent intein as provided herein. Accordingly, a hybrid protein generally comprises the structure target protein(N)-intein-target protein(C). In some embodiments, a hybrid protein is encoded by a recombinant nucleic acid, in which a nucleic acid sequence encoding an intein is inserted in frame into a nucleic acid sequence encoding a target protein. In certain embodiments, the target protein exhibits a desired activity or property that is absent or reduced in the hybrid protein. In some embodiments, excision of the intein from the hybrid protein results in a restoration of the desired activity or property in the mature, spliced target protein. Non-limiting examples of desired activities or properties of target proteins are binding activities, enzymatic activities, reporter activities (e.g., fluorescent activity), therapeutic activity, size, charge, hydrophobicity, hydrophilicity, or 3D-structure. In some embodiments, excision of the intein from a hybrid protein results in a mature, spliced target protein that exhibits the same or similar levels of a desired activity as the native target protein. A hybrid protein may be created from any target protein by embedding an intein sequence into the amino acid sequence of the target protein, for example, by generating a recombinant, hybrid protein-encoding nucleic acid molecule and subsequent transcription and translation, or by protein synthesis methods known to those of skill in the art.

The term "intein," as used herein, refers to an amino acid sequence that is able to excise itself from a protein and to rejoin the remaining protein segments (the exteins) with a peptide bond in a process termed protein splicing. Inteins are analogous to the introns found in mRNA. Many naturally occurring and engineered inteins and hybrid proteins comprising such inteins are known to those of skill in the art and the mechanism of protein splicing has been the subject of extensive research. As a result, methods for the generation of hybrid proteins from naturally occurring and engineered inteins are well known to the skilled artisan. For an overview, see pages 1-10, 193-207, 211-229, 233-252, and 325-341 of Gross, Belfort, Derbyshire, Stoddard, and Wood (Eds.) *Homing Endonucleases and Inteins* Springer Verlag Heidelberg, ISBN 9783540251064; the contents of which are incorporated herein by reference for disclosure of inteins and methods of generating hybrid proteins comprising natural or engineered inteins. As will be apparent to those of skill in the art, an intein may catalyze protein splicing in a variety of extein contexts. Accordingly, an intein can be introduced into virtually any target protein sequence to create a desired hybrid protein, and the invention is not limited in the choice of target proteins.

The term "intein domain," as used herein, refers to the amino acid sequence of an intein that is essential for self-excision and extein ligation. For example, in some inteins, the entire intein amino acid sequence, or part(s) thereof, may constitute the intein domain, while in ligand-dependent inteins, the ligand-binding domain is typically embedded into the intein domain, resulting in the structure intein domain (N)-ligand-binding domain-intein domain (C).

The term "ligand binding domain," as used herein, refers to a peptide or protein domain that binds a ligand. A ligand binding domain may be a naturally occurring or an engineered domain. Examples of ligand-binding domains referred to herein are the ligand binding domain of a native estrogen receptor, e.g., the ligand-binding domain of the native human estrogen receptor, and engineered, evolved, or mutated derivatives thereof. Typically, a ligand-binding domain useful in the context of ligand-dependent inteins, as provided herein, exhibits a specific three-dimensional structure in the absence of the ligand, which inhibits intein self-excision, and undergoes a conformational change upon binding of the ligand, which promotes intein self-excision. Some of the ligand-dependent inteins provided herein comprise a ligand-binding domain derived from the estrogen receptor that can bind 4-HT and other estrogen-receptor ligands, e.g., ligands described in more detail elsewhere herein, and undergo a conformational change upon binding of the ligand. An appropriate ligand may be any chemical compound that binds the ligand-binding domain and induces a desired conformational change. In some embodiments, an appropriate ligand is a molecule that is bound by the ligand-binding domain with high specificity and affinity. In some embodiments, the ligand is a small molecule. In some embodiments, the ligand is a molecule that does not naturally occur in the context (e.g., in a cell or tissue) that a ligand-dependent intein is used in. For example, in some embodiments, the ligand-binding domain is a ligand-binding domain derived from an estrogen receptor, and the ligand is tamoxifen or a derivative or analog thereof (e.g., hydroxytamoxifen, 4-HT).

The term "ligand-dependent intein," as used herein refers to an intein that comprises a ligand-binding domain. Typically, the ligand-binding domain is inserted into the amino acid sequence of the intein, resulting in a structure intein (N)-ligand-binding domain-intein (C). Typically, ligand-dependent inteins exhibit no or only minimal protein splicing activity in the absence of an appropriate ligand, and a marked increase of protein splicing activity in the presence of the ligand. In some embodiments, the ligand-dependent intein does not exhibit observable splicing activity in the absence of ligand but does exhibit splicing activity in the presence of the ligand. In some embodiments, the ligand-dependent intein exhibits an observable protein splicing activity in the absence of the ligand, and a protein splicing activity in the presence of an appropriate ligand that is at least 5 times, at least 10 times, at least 50 times, at least 100 times, at least 150 times, at least 200 times, at least 250 times, at least 500 times, at least 1000 times, at least 1500 times, at least 2000 times, at least 2500 times, at least 5000 times, at least 10000 times, at least 20000 times, at least 25000 times, at least 50000 times, at least 100000 times, at least 500000 times, or at least 1000000 times greater than the activity observed in the absence of the ligand. In some embodiments, the increase in activity is dose dependent over at least 1 order of magnitude, at least 2 orders of magnitude, at least 3 orders of magnitude, at least 4 orders of magnitude, or at least 5 orders of magnitude, allowing for fine-tuning of intein activity by adjusting the concentration of the ligand.

The term "mutation," as used herein, refers to an alteration, for example, a deletion, substitution, addition, inversion, duplication, or multiplication of a residue or a plurality of residues, in a sequence of residues, for example, in a nucleic acid or peptide sequence. For example, in some embodiments, the term mutation refers to a substitution of an amino acid residue of a protein, e.g., a ligand-dependent intein, with a different amino acid residue. In some embodiments, the term mutation refers to a substitution of a nucleotide residue of a nucleic acid molecule, e.g., a nucleic acid molecule encoding a ligand-dependent intein, with a different nucleotide. In some such embodiments, the mutation in the intein-encoding nucleic acid results in a substitution of an amino acid in the encoded protein.

The terms "nucleic acid," "nucleic acid molecule," and "polynucleotide" are used interchangeably herein, and refer to a polymer of ribonucleotides (RNA molecules) or deoxyribonucleotides (DNA molecules) in either single-stranded, or double-stranded form. Double-stranded DNA-DNA, DNA-RNA and RNA-RNA helices are possible. The term nucleic acid molecule refers to the primary and secondary structure of the molecule, and does not limit it to any particular tertiary forms. Thus, these term include, for example, double-stranded DNA found in linear (e.g., restriction fragments) or circular DNA molecules, plasmids, and chromosomes. Nucleotide sequences of nucleic acid molecules are described in 5'-to-3' direction.

The terms "peptide" and "protein" are used interchangeably herein and refer to a molecule that comprises a polymer of at least three amino acids linked together by peptide (amide) bonds. Peptides can comprise natural amino acids, non-natural amino acids, and/or amino acid analogs. A peptide may comprise an amino acid that is modified, for example, by the addition of a chemical entity such as a carbohydrate group, a phosphate group, a farnesyl group, an isofarnesyl group, a fatty acid group, a linker for conjugation, functionalization, or other modification (e.g., amidation). In some embodiments, a peptide comprising an amino acid modification exhibits an increased stability or biological activity as compared to its unmodified counterpart. Peptide sequences are given by convention starting with the amino-terminus (N-terminus, N) and ending with the carboxy-terminus (C-terminus, C).

The term "protein splicing," as used herein, refers to a process in which a sequence, an intein, is excised from within an amino acid sequence, and the remaining fragments of the amino acid sequence, the exteins, are ligated via an amide bond to form a continuous amino acid sequence.

The term "small molecule," as used herein, refers to a non-peptidic, non-oligomeric organic compound either prepared in the laboratory or found in nature. Small molecules, as used herein, can refer to compounds that are "natural product-like", however, the term "small molecule" is not limited to "natural product-like" compounds. Rather, a small molecule is typically a non-polymeric, non-oligomeric molecule that is characterized in that it contains several carbon-carbon bonds, and has a molecular weight of less than 2000 g/mol, preferably less than 1500 g/mol, although this characterization is not intended to be limiting for the purposes of the present invention.

DETAILED DESCRIPTION OF CERTAIN EMBODIMENTS OF THE INVENTION

Protein splicing elements known as inteins are able to catalyze their excision out of a single polypeptide and leave behind the flanking sequences, or exteins, precisely ligated together through a native peptide bond (Paulus, 2000). Inteins are attractive tools for modulating protein expression because they do not require any other cellular components, are able to splice out of a wide variety of extein contexts (Xu et al., 1993), and can undergo splicing in minutes (Paulus, 2000). Although natural inteins splice spontaneously, inteins that undergo splicing in a small molecule-dependent manner have been developed by fusing intein halves with proteins that dimerize in the presence of a small molecule (Mootz and Muir, 2002; Mootz et al., 2003; Shi and Muir, 2005), or by directed evolution in which a library of intact inteins fused to a ligand-binding domain was screened to splice in the presence, but not the absence, of a small molecule (Buskirk et al., 2004). These small molecule-dependent inteins have enabled protein function in cells to be controlled post-translationally by the addition of an exogenous, cell-permeable molecule (Mootz and Muir, 2002, Mootz et al., 2003, Buskirk et al., 2004; Mootz et al., 2004; Shi and Muir, 2005; Yuen et al., 2006; Schwartz et al., 2007; Hartley and Madhani, 2009). For example, in some embodiments, a hybrid protein comprising a ligand-dependent intein embedded into the amino acid sequence of a target protein is expressed in a cell, for example, a human cell, in the absence of an appropriate ligand. If the intein disrupts the activity of the target protein, and no native target protein is present in the cell, then there is no target protein present in the cell. In some embodiments, the cell is contacted with an appropriate ligand activating the ligand-dependent intein. As a result, the intein self-excises from the hybrid protein, generating a mature, spliced target protein. In some embodiments, this protein splicing restores the activity of the target protein. To give but one example, if the target protein is a fluorescent protein, cells expressing the hybrid protein in the absence of ligand are non-fluorescent, while fluorescence can be observed in cells contacted with ligand.

Previously, variants of the *Mycobacterium tuberculosis* RecA intein were developed that selectively splice in the presence of the cell-permeable small molecule 4-hydroxytamoxifen (4-HT) in a rapid, dose-dependent manner using directed evolution in *S. cerevisiae* (Buskirk et al., 2004). The *M. tuberculosis* RecA intein was chosen because it can efficiently splice in a wide variety of contexts (Lew and Paulus, 2002), and the evolved 4-HT-triggered inteins retained this characteristic. These evolved inteins have been successfully used as a tool to study the role of histone H2A.Z in establishing chromatin architecture around promoter regions in *S. cerevisiae* (Hartley and Madhani, 2009). It will be appreciated by those of skill in the art that other inteins can also be evolved according to methods described herein and the invention is not limited in this respect.

It was demonstrated that these evolved inteins are functional in mammalian cells at 37° C. but splice with significantly reduced speed, lower efficiency, and higher background splicing in the absence of 4-HT compared with splicing at 30° C. in yeast (Yuen et al., 2006). These limitations constrain the utility of these evolved inteins as tools for mammalian cell biology; indeed, only two studies (Mootz et al., 2003; Yuen et al., 2006) have reported the use of small molecule-dependent inteins in mammalian cells.

This invention relates to the development of improved ligand-dependent intein and intein domain variants that can splice efficiently, rapidly, and/or in a ligand-dependent manner at about 37° C., for example, in cells of higher eukaryotes (e.g., mammalian cells). Results of new directed evolution efforts to improve the splicing characteristics of 4-HT dependent inteins for use at about 37° C. and in mammalian cells are described herein. The resulting second-generation inteins in yeast cells exhibit substantially improved splicing activity and speed with no significant increase in background splicing at both 30° C. and 37° C. These second-generation inteins also splice with much greater speed and efficiency in mammalian cells, for example, in human cells, at 37° C. in four different extein contexts compared with the parental inteins.

These new ligand-dependent inteins represent more effective and broadly applicable tools for the small-molecule triggered, post-translational modulation of protein activities in living systems including mammalian cells.

Ligand-Dependent Inteins

Inteins are polypeptide sequences embedded within a protein. Inteins catalyze their own excision from the peptide chain and ligation of the resulting ends of the protein. The self-excision catalyzed by the intein results in a mature, spliced protein and a free intein. While naturally-occurring inteins catalyze protein splicing in a spontaneous manner, the splicing activity of the inteins provided herein is dependent on a ligand, for example, a small molecule ligand.

The ligand-dependent inteins provided herein comprise a modified ligand-binding domain of the estrogen receptor protein, embedded into a modified RecA intein from *M. tuberculosis*. In some embodiments, the ligand-binding domain is derived from the an estrogen receptor protein, for example, from the human estrogen receptor. The sequence of the human estrogen receptor and the location of the ligand-binding domain within the human estrogen receptor protein are well known to those of skill in the art. Non-limiting, exemplary sequences of the human estrogen receptor can be retrieved from RefSeq database entries NP_000116 (isoform 1); NP_001116212 (isoform 2); NP_001116213 (isoform 3); and NP_001116214 (isoform 4) from the National Center for Biotechnology Information (NCBI, www.ncbi.nlm.nih.gov). In some embodiments, the ligand-binding domain of a ligand-dependent intein provided herein is derived from a sequence comprising amino acid residues 304-551 of the human estrogen receptor.

It will be appreciated by those of skill in the art that other ligand binding domains are also useful in connection with the intein domains described herein. For example, some aspects of this invention provide ligand-dependent inteins that comprise an N-terminal and a C-terminal intein domain as described herein, and a central ligand-binding domain, for example, a ligand-binding domain of a hormone-binding protein, e.g., of an androgen receptor, an estrogen receptor, an ecdysone receptor, a glucocorticoid receptor, a mineralocorticoid receptor, a progesterone receptor, a retinoic acid receptor, or a thyroid hormone receptor protein. Ligand-binding domains of hormone-binding receptors, inducible fusion proteins comprising such ligand-binding domains, and methods for the generation of such fusion proteins are well known to those of skill in the art (see, e.g., Becker, D., Hollenberg, S., and Ricciardi, R. (1989). Fusion of adenovirus E1A to the glucocorticoid receptor by high-resolution deletion cloning creates a hormonally inducible viral transactivator. *Mol. Cell. Biol.* 9, 3878-3887; Boehmelt, G., Walker, A., Kabrun, N., Mellitzer, G., Beug, H., Zenke, M., and Enrietto, P. J. (1992). Hormone-regulated v-rel estrogen receptor fusion protein: reversible induction of cell transformation and cellular gene expression. *EMBO J* 11, 4641-4652; Braselmann, S., Graninger, P., and Busslinger, M. (1993). A selective transcriptional induction system for mammalian cells based on Gal4-estrogen receptor fusion proteins. *Proc Natl Acad Sci USA* 90, 1657-1661; Furga G, Busslinger M (1992). Identification of Fos target genes by the use of selective induction systems. *J. Cell Sci. Suppl* 16, 97-109; Christopherson, K. S., Mark, M. R., Bajaj, V., and Godowski, P. J. (1992). Ecdysteroid-dependent regulation of genes in mammalian cells by a Drosophila ecdysone receptor and chimeric transactivators. *Proc Natl Acad Sci USA* 89, 6314-8; Eilers, M., Picard, D., Yamamoto, K., and Bishop, J. (1989). Chimaeras of Myc oncoprotein and steroid receptors cause hormone-dependent transformation of cells. *Nature* 340, 66-68; Fankhauser, C. P., Briand, P. A., and Picard, D. (1994). The hormone binding domain of the mineralocorticoid receptor can regulate heterologous activities in cis. *Biochem Biophys Res Commun* 200, 195-201; Godowski, P. J., Picard, D., and Yamamoto, K. R. (1988). Signal transduction and transcriptional regulation by glucocorticoid receptor-LexA fusion proteins. *Science* 241, 812-816; Kellendonk, C., Tronche, F., Monaghan, A., Angrand, P., Stewart, F., and Schutz, G. (1996). Regulation of Cre recombinase activity by the synthetic steroid RU486. *Nuc. Acids Res.* 24, 1404-1411; Lee, J. W., Moore, D. D., and Heyman, R. A. (1994). A chimeric thyroid hormone receptor constitutively bound to DNA requires retinoid X receptor for hormone-dependent transcriptional activation in yeast. *Mol Endocrinol* 8, 1245-1252; No, D., Yao, T. P., and Evans, R. M. (1996). Ecdysone-inducible gene expression in mammalian cells and transgenic mice. *Proc Natl Acad Sci USA* 93, 3346-3351; and Smith, D., Mason, C., Jones, E., and Old, R. (1994). Expression of a dominant negative retinoic acid receptor g in *Xenopus embryos* leads to partial resistance to retinoic acid. *Roux's Arch. Dev. Biol.* 203, 254-265; all of which are incorporated herein by reference in their entirety). Additional ligand-binding domains useful for the generation of ligand-dependent inteins as provided herein will be apparent to those of skill in the art and the invention is not limited in this respect.

The ligand-dependent inteins provided herein are inactive (or only minimally active) in the absence of the appropriate ligand, but can be induced to be active, and, thus, to self-excise, by contacting them with a ligand that binds the ligand-binding domain of the human estrogen receptor. Small molecule ligands binding the ligand-binding domain of the estrogen receptor (e.g., the human estrogen receptor), and thus useful to induce the activity of the ligand-dependent inteins described herein, are well known to those of skill in the art. In some embodiments, the ligand used to induce the activity of the ligand-dependent inteins described herein specifically binds to the ligand-binding domain of the estrogen receptor. In some embodiments, the ligand binds the ligand-binding domain of a ligand-dependent intein provided herein with high affinity, for example, with an affinity of at least about $10^{-10}$ M, at least about $10^{-9}$ M, at least about $10^{-8}$ M, at least about $10^{-7}$ M, at least about $10^{-6}$ M, or at least about $10^{-5}$ M. Examples of appropriate estrogen receptor-binding ligands that are useful to induce the activity of the ligand-dependent inteins provided herein, for example, the ligand-dependent inteins provided in SEQ ID NOs: 3-8, include, but are not limited to, 17β-estradiol, 17α-ethynyl estradiol, tamoxifen and tamoxifen analogs (e.g., 4-hydroxytamoxifen (4-HT, 4-OHT), 3-hydroxytamoxifen (droloxifene)), tamoxifen metabolites (e.g., hydroxytamoxifen, endoxifen), raloxifene, toremifene, ICI-182, and ICI-780. Other useful ligands will be apparent to those of skill in the art, and the invention is not limited in this respect.

In some embodiments, the ligand-dependent intein is inactive or only minimally active in the absence of an appropriate ligand. In some embodiments, the self-excision activity of the ligand-dependent intein is increased in the presence of an appropriate ligand. In some embodiments, the ligand increases the activity of a ligand-dependent intein provided herein in a concentration-dependent manner, with low ligand concentration levels translating to low intein activity levels, and high ligand concentration levels translating to high intein activity levels. In some embodiments where intein activity is induced in living cells, the concentration of the ligand and the time of exposure of the cells to the ligand are chosen to be non-toxic to the cells. Ligand may be non-toxic over a whole range of concentrations.

In some embodiments, a ligand-dependent intein provided herein does not exhibit observable splicing activity in the absence of an appropriate ligand, but does exhibit splicing activity in the presence of such a ligand. In some embodiments, a ligand-dependent intein provided herein exhibits an increase in splicing activity of at least about 5-fold, at least about 10-fold, at least about 15-fold, at least about 20-fold, at least about 25-fold, at least about 30-fold, at least about 40-fold, at least about 50-fold, at least about 75-fold, at least about 100-fold, at least about 150-fold, at least about 200-fold, at least about 250-fold, at least about 500-fold, at least about 1000-fold, at least about 2000-fold, at least about 5000-fold, at least about 10000-fold, at least about 50000-fold, at least about 100000-fold, at least about 500000-fold, or at least about 1000000 fold, in the presence of a ligand for the ligand-binding domain, e.g., 4-HT, as compared to its baseline activity in the absence of the ligand. In some embodiments, a ligand-dependent intein provided herein exhibits a level of protein splicing activity in the presence of an appropriate ligand, e.g., 4-HT, that is similar to the splicing activity of the RecA intein observed or expected under the same conditions. In some embodiments, a ligand-dependent intein provided herein exhibits a splicing activity in the presence of an appropriate ligand, e.g., 4-HT, that is greater than the splicing activity of the RecA intein observed or expected under the same conditions, for example, by a factor of at least 2, at least 3, at least, 4, at least 5, at least 6, at least 7, at least 8, at least 9, at least 10, at least 20, at least 25, at least 30, at least 40, at least 50, or at least 100.

Intein Domains

The invention provides intein domains for use in ligand-dependent intein applications at temperatures within the range of about 30° C. to about 37° C., for example, in mammalian cells that are cultured at about 37° C. In some embodiments, the optimized intein domains provided herein comprise an N-terminal intein domain and a C-terminal intein domain. To obtain a ligand-dependent intein, the N- and C-terminal intein domains are fused to a central ligand-binding domain, for example, to the ligand-binding domain of a steroid (e.g., estrogen) receptor protein. In some embodiments, the ligand-binding domain is a native ligand-binding domain, while in other embodiments, the ligand-binding domain is also optimized for use at temperatures within the range of about 30° C. to about 37° C. For example, in some embodiments, the ligand-binding domain is optimized for use in mammalian cells that are cultured at about 37° C. In some embodiments, the optimized intein domains provided herein are derived from naturally-occurring intein domains by evolution methods described herein. In some embodiments, the optimized intein domains provided herein are derived from the RecA intein domain as described in more detail herein.

In some embodiments, an intein domain is provided that comprises the sequence: CLAEGTRIFDPVTGTT HRIEDVVDGRKPIHVVAV*AKDGTLLARPVVSWFDQ GTRDV IGLRIAGGAI*VWATPDHKVLTEYGWRAA GELRKGDRVARVQAFADALDDKFLHD MLAEE*LR YSVIREVLPTRRARTFDLEVEELHTLVAEGVVVHN (SEQ ID NO: 9), wherein at least one of the amino acid residues followed by an asterisk (*) is mutated (e.g., substituted with a different amino acid residue or deleted). In some embodiments, the optimized intein domain comprises a V*→A (Valine* to Alanine) mutation, an I*→T (Isoleucine* to Threonine) mutation, and/or an E*→G (Glutamate* to Glycine) mutation. Ligand-dependent inteins comprising a ligand-binding protein domain, for example, a ligand-binding domain of the estrogen receptor, inserted into the intein domain sequence provided above, are also provided.

In some embodiments, an N-terminal intein domain (intein-N) is provided that comprises the amino acid sequence: CLAEGTRIFDPVTGTTHRIEDVVDGRKPIHVVAV*AK DGTLLARPVVSWFDQGTRDV IGLRIAGGAI*VWATP-DHKVLTEYGWRAAGELRKGDRVA (SEQ ID NO: 10), wherein at least one of the amino acid residues followed by an asterisk is mutated. In some embodiments, the N-terminal intein domain comprises a V*→A mutation and/or an I*→T mutation.

In some embodiments, an optimized C-terminal intein domain (intein-C) is provided that comprises the amino acid sequence: RVQAFADALDDKFLHDMLAEE*LRYSVIREVLPTRRA RTFDLEVEELHTLVAEGVVV HN (SEQ ID NO: 11), wherein the E* residue is mutated. In some embodiments, the mutation is an E*G mutation. In some embodiments, a ligand-dependent intein is provided that comprises the N-terminal intein domain and/or the C-terminal intein domain described above, and a ligand-binding domain, for example, a ligand-binding domain of the steroid (e.g., estrogen) receptor as described herein. In some embodiments, a ligand-dependent intein is provided that comprises the N-terminal and the C-terminal intein domains described above and a central ligand-binding domain. In some embodiments, the ligand-binding domain is a ligand-binding domain described herein, for example, the ligand-binding domain of an estrogen receptor protein, or an optimized, mutated derivative thereof. In some embodiments, the ligand-binding domain comprises the amino acid sequence: NSLALSLTADQMVSALLDAEP-PILYSEYDPTSPFSEASMMGLLTNLADRELVHMINW AKRVPGFVDLTLHDQAHLLECAWLEILM-IGLVWRSMEHPGKLLFAPNLLLDRNQGK CVEGMVE-IFDMLLATSSRFRMMNLQGEEFVCLKSI-ILLNSGVYTFLSSTLKSLEEKDH IHRALDKITDTLIHLMAKA-GLTLQQQHQRLAQLLLILSHIRHMSNKG-MEHLYSMKYT NVVPLYDLLLEMLDAHRLHA (SEQ ID NO: 12). In some embodiments, the ligand-binding domain comprises the amino acid sequence: NSLALSLTADQMVSALLDAEPPIL*YSEYD*PTSPFSE ASMMGLLTNLADRELVHMIN WAKRVPGFVD LTLHDQAHLLEC*AWLEILMIGLVWRSMEHPGKLLF APNLLLDRNQ GKCVEGMVEIFDMLLATSSRFRMMN-LQGEEFVCLKSIILLNSGVYTFLSSTLKSLEEK DHI-HRALDKITDTLIHLMAKAGLTLQQQHQR-LAQLLLILSHIRHMSNKGMEHLYSMK YT*NVVPLYDLLLEMLDAHRLHA (SEQ ID NO: 13), wherein at least one of the residues L*, D*, C*, or T* is mutated. In some embodiments, the ligand-binding domain comprises an L*→P (Leucine* to Proline), a D*→N (Aspartate* to Asparagine), a C*→R (Cysteine* to Arginine), and/or a T*→K (Threonine* to Lysine) mutation.

Ligand-Binding Domain

The invention also provides ligand-binding protein domains. The ligand-binding domains provided herein are derived from the human estrogen receptor ligand-binding domain and can be used to generate ligand-dependent proteins, for example, ligand-dependent inteins. Useful ligands that bind to the ligand-binding domains provided herein are described in more detail elsewhere herein. Non-limiting examples of such ligands include tamoxifen and tamoxifen analogs and derivatives (e.g., 4-HT).

Some embodiments provide a ligand-binding protein domain comprising the amino acid sequence: NSLALSLTADQMVSALLDAEPPIL*YSEYD*PTSPFSE ASMMGLLTNLADRELVHMIN WAKRVPGFVDLT LHDQAHLLEC*AWLEILMIGLVWRSMEHPGKLLFAP NLLLDRNQ GKCVEGMVEIFDMLLATSSRFRMMN-LQGEEFVCLKSIILLNSGVYTFLSSTLKSLEEK DHI-HRALDKITDTLIHLMAKAGLTLQQQHQR-LAQLLLILSHIRHMSNKGMEHLYSMK YT*NVVPLYDLLLEMLDAHRLHA (SEQ ID NO: 13). In some embodiments, at least one of the residues L*, D*, C*, or T* is mutated. In some embodiments, the estrogen-binding domain comprises an L*P, a D*N, a C*R, and/or a T*K mutation. In some embodiments, the ligand-binding domain comprises the ligand-binding domain provided in any of SEQ ID NOs 3-8. The ligand-binding domain in SEQ ID NOs 3-8 can be identified by those of skill in the art, for example, by sequence alignment of any of the sequences in SEQ ID NOs 3-8 with the ligand-dependent domain provided above.

In some embodiments, a ligand-binding domain described herein is fused to an N-terminal intein domain and a C-terminal intein domain, thus forming a ligand-dependent intein of the structure intein(N)-ligand-binding domain-intein(C). In some embodiments, the C-terminal and/or the N-terminal intein domain is a naturally occurring intein domain. Naturally occurring intein domains are well known to those of skill in the art (e.g., as described in International PCT Patent Application, Serial Number PCT/US2005/010805, filed Mar. 30, 2005; U.S. Pat. No. 7,192,739, issued Mar. 20, 2007; U.S. Pat. No. 7,541,450, issued Jun. 2, 2009; and on pages 1-10, 193-207, 211-229, 233-252, and 325-341 of Gross, Belfort, Derbyshire, Stoddard, and Wood (Eds.) *Homing Endonucleases and Inteins* Springer Verlag Heidelberg, ISBN 9783540251064; the contents of each of which are incorporated herein by reference), and the invention is not limited in this respect.

In some embodiments, the ligand-binding domain is embedded in the intein between the N- and the C-terminal intein domains. In other embodiments, the ligand-binding domain is embedded anywhere in the intein amino acid sequence.

In some embodiments, an ligand-binding domain described herein (e.g., a human estrogen receptor-derived ligand-binding domain) is fused to a RecA-derived intein domain, for example, an intein domain as described herein. In some embodiments, an estrogen-binding domain described herein, for example, the estrogen-binding domain provided in any of SEQ ID NOs 3-8 are fused to an N-terminal and a C-terminal intein domain as provided herein (e.g., the intein domain provided in any of SEQ ID NOs: 3-8).

In some embodiments, a ligand-binding domain, e.g., an estrogen-binding domain, provided herein is fused to an N-terminal and a C-terminal intein sequence as provided in any one of SEQ ID NOs: 3-8 to generate a ligand-dependent intein of the structure intein(N)-ligand-binding domain-intein(C). For example, in such embodiments, the estrogen-binding domain of SEQ ID NO: 3 is fused to the N-terminal and the C-terminal intein domains of SEQ ID NO: 4. In some other such embodiments, the estrogen-binding domain of SEQ ID NO: 3 is fused to the N-terminal and the C-terminal intein domains of SEQ ID NO: 5. In some other such embodiments, the estrogen-binding domain of SEQ ID NO: 7 is fused to the N-terminal and the C-terminal intein domains of SEQ ID NO: 6, and so on.

In some embodiments, an estrogen-binding domain provided herein is fused to an N-terminal intein domain as provided in any of SEQ ID NOs: 3-8, and to a C-terminal intein sequence as provided in any of SEQ ID NOs: 3-8, wherein the N-terminal and the C-terminal intein domains are not from the same SEQ ID NO. For example, in some such embodiments, the estrogen-binding domain of SEQ ID NO: 5 is fused to the N-terminal intein of SEQ ID NO: 3 and to the C-terminal intein domains of SEQ ID NO: 4. In some other such embodiments, the estrogen-binding domain of SEQ ID NO: 3 is fused to the N-terminal intein domain of SEQ ID NO: 6 and the C-terminal intein domains of SEQ ID NO: 7. In some other such embodiments, the estrogen-binding domain of SEQ ID NO: 7 is fused to the N-terminal intein domain of SEQ ID NO: 7 and the C-terminal intein domains of SEQ ID NO: 3, and so on.

In some embodiments, a ligand-binding domain provided herein is fused to an N-terminal intein domain and a C-terminal intein domain, forming a ligand-dependent intein. In some embodiments, the N-terminal intein domain comprises the sequence CLAEGTRIFDPVTGTTHRIEDVVDGRKPIHVVAV*AK DGTLLARPVVSWFDQGTRDV IGLRIAGGAI*VWATP DHKVLTEYGWRAAGELRKGDRVA (SEQ ID NO: 10). In some embodiments, the N-terminal intein sequence comprises the sequence above with a mutation of the V* and/or the I* residue(s). In some embodiments, the N-terminal intein sequence comprises the sequence above with a V*→A, and/or an I*→T mutation. In some embodiments, the C-terminal intein domain comprises the sequence RVQAFADALDDKFLHDMLAEE*LRYSVIREVLPTRR ARTFDLEVEELHTLVAEGVVV HN (SEQ ID NO: 11). In some embodiments, the C-terminal intein sequence comprises the sequence above with a mutation of the E* residue. In some embodiments, the C-terminal intein sequence comprises the sequence above with an E*→G mutation.

Ligand-Dependent Inteins

The invention provides ligand-dependent inteins that are optimized for use at temperatures within the range of about 30° C. to about 42° C., for example, for use at about 37° C. Some of the optimized inteins provided herein comprise a RecA-derived intein domain and a ligand-binding domain and are of the general structure intein(N)-ligand-binding domain-intein(C). Some of the optimized inteins provided herein are derived from the 3-2 intein as described in detail in International PCT Patent Application Serial Number PCT/US2005/010805, filed Mar. 30, 2005; U.S. Pat. No. 7,192,739, issued Mar. 20, 2007; and U.S. Pat. No. 7,541,450, issued Jun. 2, 2009; all of which are entitled "Ligand-dependent Protein Splicing," and the entire contents of each of which are incorporated herein by reference. The 3-2 intein was derived from the 2-4 intein, also described in the above-referenced US patents.

The inteins provided herein are optimized for use at temperatures within the range of about 30° C. to about 37° C., for example, in mammalian cells that are cultured at about 37° C. The provided intein sequences are universally applicable to regulate the activity of any target protein post-translationally, since they can be inserted into any target protein to generate an inactive hybrid protein that can be spliced in a ligand-dependent manner to restore target protein activity, as described in more detail elsewhere herein.

In some embodiments, the optimized intein sequence comprises the amino acid sequence of the 30R3-1 intein (mutations as compared to the 3-2 intein sequence are underlined):

```
                                               (SEQ ID NO: 3)
CLAEGTRIFDPVTGTTHRLEDVVDGRKPIHVVAAAKDGTLLARPVVSWFD

QGTRDVIGLRIAGGATVWATPDHKVLTEYGWRAAGELRKGDRVAGPGGSG

NSLALSLTADQMVSALLDAEPPIPYSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL
```

-continued

LNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGG

SGASRVQAFADALDDKFLHDMLAEGLRYSVIREVLPTRRARTFDLEVEEL

HTLVAEGVVVHNC.

In some embodiments, an intein is provided that comprises or consists of the amino acid sequence of the 30R3-2 intein:

(SEQ ID NO: 4)
CLAEGTRIFDPVTGTTHRIEDVVDGRKPIHVVAAAKDGTLLARPVVSWFD

QGTRDVIGLRIAGGATVWATPDHKVLTEYGWRAAGELRKGDRVAGPGGSG

NSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGG

SGASRVQAFADALDDKFLHDMLAEELRYSVIREVLPTRRARTFDLEVEEL

HTLVAEGVVVHNC.

In some embodiments, an intein is provided that comprises or consists of the amino acid sequence of the 30R3-3 intein:

(SEQ ID NO: 5)
CLAEGTRIFDPVTGTTHRIEDVVDGRKPIHVVAAAKDGTLLARPVVSWFD

QGTRDVIGLRIAGGATVWATPDHKVLTEYGWRAAGELRKGDRVAGPGGSG

NSLALSLTADQMVSALLDAEPPIPYSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGG

SGASRVQAFADALDDKFLHDMLAEELRYSVIREVLPTRRARTFDLEVEEL

HTLVAEGVVVHNC.

In some embodiments, an intein is provided that comprises or consists of the amino acid sequence of the 37R3-1 intein:

(SEQ ID NO: 6)
CLAEGTRIFDPVTGTTHRIEDVVDGRKPIHVVAAAKDGTLLARPVVSWFD

QGTRDVIGLRIAGGATVWATPDHKVLTEYGWRAAGELRKGDRVAGPGGSG

NSLALSLTADQMVSALLDAEPPILYSEYNPTSPFSEASMMGLLTNLADRE

LVHMINWAKRVPGFVDLTLHDQAHLLERAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGG

SGASRVQAFADALDDKFLHDMLAEGLRYSVIREVLPTRRARTFDLEVEEL

HTLVAEGVVVHNC.

In some embodiments, an intein is provided that comprises or consists of the amino acid sequence of the 37R3-2 intein:

(SEQ ID NO: 7)
CLAEGTRIFDPVTGTTHRIEDVVDGRKPIHVVAAAKDGTLLARPVVSWFD

QGTRDVIGLRIAGGATVWATPDHKVLTEYGWRAAGELRKGDRVAGPGGSG

NSLALSLTADQMVSALLDAEPPILYSEYDPTSPFSEASMMGLLTNLADRE

LVHMINWAKRVPGFVDLTLHDQAHLLERAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGG

SGASRVQAFADALDDKFLHDMLAEELRYSVIREVLPTRRARTFDLEVEEL

HTLVAEGVVVHNC.

In some embodiments, an intein is provided that comprises or consists of the amino acid sequence of the 37R3-3 intein:

(SEQ ID NO: 8)
CLAEGTRIFDPVTGTTHRIEDVVDGRKPIHVVAVAKDGTLLARPVVSWFD

QGTRDVIGLRIAGGATVWATPDHKVLTEYGWRAAGELRKGDRVAGPGGSG

NSLALSLTADQMVSALLDAEPPILYSEYDPTSPFSEASMMGLLTNLADRE

LVHMINWAKRVPGFVDLTLHDQAHLLERAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGG

SGASRVQAFADALDDKFLHDMLAEELRYSVIREVLPTRRARTFDLEVEEL

HTLVAEGVVVHNC.

In some embodiments, a ligand-dependent intein is provided, wherein the intein does not comprise a sequence as provided in SEQ ID NO: 1 or SEQ ID NO:2, and wherein the intein comprises an amino acid sequence at least 90%, at least 95%, at least 98%, or at least 99% identical to any of the amino acid sequences provided in SEQ ID NOs 3-8. The level of sequence identity can be determined by methods known to those of skill in the art, for example, by sequence alignment. In some embodiments, the term at least 99% sequence identity refers to a level of identity between two sequences (e.g., amino acid sequences), in which at least 99 out of 100 residues (e.g., amino acid residues) are identical, if the sequences are optimally aligned. The optimal alignment of two sequences is typically the alignment in which a maximum number of residue identity matches is observed between the two sequences.

Hybrid Protein

The ligand-dependent inteins provided herein have the ability to excise themselves from a target protein they are embedded in, and to ligate the resulting ends of the protein together, resulting in a mature, spliced protein and a free intein. A protein comprising a target protein sequence and, integrated into this sequence, an intein sequence, is referred to herein as a hybrid protein. In some embodiments, a hybrid protein is provided that comprises an intein or intein domain described herein, for example, a ligand-dependent intein provided in any of SEQ ID NOs: 3-8. Typically, the ligand-dependent intein sequence is integrated into a target protein sequence to form the hybrid protein structure target protein (N)-intein (N)-ligand binding domain-intein (C)-target protein (C). In some embodiments, the intein is inserted into an α-helical region of the target protein. In some embodiments, the intein is inserted into a β-strand of the target protein. In some embodiments, in the presence of an appropriate ligand binding the ligand-dependent intein, the ligand dependent intein catalyzes the excision of the ligand-dependent intein and ligation of the target protein forming the mature, spliced target protein of the structure target (N)-target (C). In some embodiments, the hybrid protein does not exhibit a function of the native target protein. In some embodiments, a function of the target protein is disrupted or diminished by the inserted intein sequence. In some embodiments, excision of the intein from the hybrid protein restores target protein function in the spliced, mature target protein. In some embodiments, the ligand is HT-4.

For example, in some embodiments, a ligand-dependent intein as provided herein is embedded in a reporter protein (target protein), for example, a fluorescent protein (e.g., GFP), and the resulting hybrid protein does not exhibit fluorescence or only minimal fluorescence as compared to the native reporter protein. In some embodiments, the mature, spliced reporter protein, now devoid of the intein, exhibits similar or only slightly decreased reporter activity (e.g., fluorescence) as compared to the native reporter protein.

In some embodiments, the function of the target protein is fully restored upon ligand-induced self-excision of the ligand-dependent intein from the target protein. In some embodiments, the function of the target protein is restored to a significant extent upon ligand-induced self-excision of the ligand-dependent intein from the target protein. For example, in some embodiments, the mature, spliced target protein exhibits at least about 80%, at least about 90%, at least about 95%, at least about 98%, at least about 99%, or at least about 100% of the activity exhibited by the native target protein.

In some embodiments, the self-excision of a ligand-dependent intein provided herein leaves no "scar" or only a minimal "scar" in the resulting intein-free protein. For example, in some embodiments, the splicing reaction either leaves no amino acid residue from the intein sequence or just a short sequence of one, two, or three amino acid residues. In certain embodiments, the splicing reaction leaves no amino acid residues from the intein in the mature protein after self-excision. In other embodiments, the splicing reaction leaves one amino acid residue from the intein, for example, a cysteine residue. In some embodiments, the amino acid residue(s) from the intein left in the mature, spliced protein do(es) not interfere, or interfere(s) only minimally, with the activity of the mature, spliced protein, e.g., does not inhibit an activity of interest exhibited by the mature, spliced protein as compared to the native target protein.

Target Proteins

The ligand-dependent inteins provided herein can be inserted into any target protein to create a hybrid protein of the structure target protein (N)-intein-target protein(C). Such engineered hybrid proteins can be synthesized de novo by protein synthesis well known to those of skill in the art, for example, by solid phase peptide synthesis methods (e.g., Fmoc synthesis), or by generating a nucleic acid encoding the desired hybrid protein, for example, by recombinant nucleic acid generation methods well known to those of skill in the art (e.g., restriction cloning, PCR, and/or gene synthesis methods).

In some embodiments, the intein self-excises efficiently only if the first residue of the C-terminal extein (e.g., target protein(C) in the structure described above) is a specific amino acid residue, for example, a cysteine. In some embodiments, an intein is inserted into a target protein at a position immediately upstream (N-terminal) of such a residue (e.g., a cysteine residue). If inserted into such a position, the intein will leave no "scar" in the protein after excision, since the excision will leave the first extein residue, which, in this case, is a residue of the native protein. In other embodiments, where no suitable residue (e.g., a cysteine residue) can be identified for upstream intein insertion, a sequence comprising the intein domain and an additional, C-terminal amino acid residue (e.g., a C-terminal cysteine residue), may be inserted into the desired sequence position of the target protein. In such cases, intein excision will leave the first extein residue (e.g., the C-terminal cysteine residue) inserted in the target protein. Those of skill in the art will be able to identify suitable residues that can serve as first C-terminal extein residues, and devise strategies for inserting suitable C-terminal amino acid residues with the intein domains in those embodiments, where suitable first C-terminal extein residues are not available in the native target protein sequence.

Any protein can be modified to comprise an intein and, thus, serve as a target protein. In some embodiments the target protein is a protein the ligand-dependent activation of which is useful for a therapeutic, diagnostic, or experimental purpose. In certain embodiments, the target protein exhibits an activity in a cell or in a biochemical pathway being studied. In other embodiments, the target protein is a therapeutic protein. In certain embodiments, the target protein is an enzyme (e.g., an oxidoreductase, a transferase, a hydrolase, a lyase, an isomerase, or a ligase, such as a kinase, a phosphorylase, a cytochrome p450 enzyme, a protease, a polymerase, an aldolase, or a phosphatase). In other embodiments, the target protein is involved in a cell signaling pathway. In certain embodiments, the target protein is a kinase. In certain embodiments, the target protein is a transcription factor. In certain embodiments, the target protein is a transmembrane signaling protein. In some embodiments, the target protein is a recombinase. In some embodiments, the target protein is an endonucleases, for example, a zinc finger nuclease. In certain embodiments, the target protein is a receptor. In other embodiments, the target protein is a structural protein. In some embodiments, the target protein is a reporter protein. In some embodiments, the target protein is a fluorescent protein. In some embodiments, the target protein is GFP, RFP, BFP, CFP, YFP, or any enhanced or destabilized variant thereof. In some embodiments, the target protein is a mitochondrial protein. In some embodiments, the target protein is a fusion of one or more proteins or protein domains.

Typically, the target protein exhibits a biological activity that is disrupted when the ligand-dependent intein is inserted into the target protein. In some embodiments, the resulting hybrid protein does not exhibit the biological activity of the target protein. In some embodiments, the hybrid protein exhibits a diminished level of the biological activity as compared to the native target protein. In some embodiments, once the intein is excised during protein splicing, the biological activity is restored in the mature, spliced target protein. In some embodiments, the hybrid protein containing a ligand-dependent intein inserted into the sequence of a target protein is inactive until it is contacted with an appropriate ligand which binds to the intein is added. In some embodiments, ligand binding induces the protein splicing activity of the ligand-dependent intein, which causes the excision of the intein and ligation of the resulting ends to form the mature, biologically active target protein.

Intein-Encoding Nucleic Acid Molecules

Some aspects of this invention provide nucleic acid molecules encoding the ligand-dependent inteins, optimized intein domains, or optimized ligand-binding domains described herein. Such nucleic acid molecules can be generated for a known intein amino acid sequence by methods well known to those of skill in the art, for example, by recombinant DNA technology methods (see, e.g., *Molecular Cloning: A Laboratory Manual*, 2nd Ed., Sambrook, Fritsch, and Maniatis (Cold Spring Harbor Laboratory Press: 1989); *Nucleic Acid Hybridization* (B. D. Hames & S. J. Higgins eds. 1984); *Methods in Enzymology* (Academic Press, Inc., N.Y.); *Immunochemical Methods in Cell and Molecular Biology* (Mayer and Walker, Academic Press, London, 1987); Ausubel et al., *Current Protocols in Molecular Biology* (John Wiley & Sons, Inc., New York, 1999); the entire contents of each of which are incorporated herein by reference). In certain embodiments, a nucleic acid molecule encoding a ligand-dependent intein as provided herein is synthesized using a DNA synthesizer. In other embodiments, the nucleic acid molecule may be excised from a vector, for example, a plasmid, or artificial chromosome comprising the intein sequence (e.g., using restriction enzymes). In some embodiments, polymerase chain reaction (PCR) is used to isolate and amplify the desired sequence. The nucleic acid molecule may also be prepared with a mutation in the sequence. In certain embodiments, codon usage may be optimized for expression in a particular organism, for example, in *E. coli, S. cerevisiae*, mouse, rat, or human. Methods for generating, deriving, and synthesizing nucleic acid molecules encoding a known amino acid sequence, and/or optimizing codon usage for an organism of interest, are well known to those of skill in the art and the invention is not limited in this respect.

Cells and Organisms

Some aspects of this invention provide cells comprising a nucleic acid encoding a ligand-dependent intein, a hybrid protein, an intein domain, or a ligand-binding domain, as described herein. In some embodiments, the nucleic acid comprises a sequence encoding a hybrid protein comprising a target protein of interest and, embedded in the target protein sequence, a ligand-dependent intein as provided herein. In some embodiments, the cell is a mammalian cell. In some embodiments, the cell is a bacterial cell. In some embodiments, the cell is a yeast cell. In some embodiments, the cell is a human cell, a mouse cell, a rat cell, a hamster cell, a pig cell, a goat cell, a cow cell, a horse cell, a cat cell, or a dog cell. In some embodiments, the cell is an embryonic stem cell. In some embodiments, the cell is a differentiated cell. In some embodiments, the cell is derived from a diseased cell or tissue, for example, from a malignant cell or tissue.

Some embodiments provide organisms comprising a cell or consisting of cells comprising an intein, comprising a nucleic acid encoding a ligand-dependent intein, a hybrid protein, an intein domain, or a ligand-binding domain, as described herein. For example, in some embodiments, a transgenic organism is provided that comprises at least one cell, in which a nucleic acid molecule encoding a ligand-dependent intein, a hybrid protein, an intein domain, or a ligand-binding domain, as described herein, is integrated into the cellular genome. In some embodiments, the transgene encodes a hybrid protein of a target protein and a ligand-dependent intein as described herein. In some embodiments, the organism does not express the native target protein in a cell or tissue of interest. For example, in some embodiments, the organism is an organism in which one or both native alleles of the target protein have been rendered non-functional by methods known to those of skill in the art, for example, by knockout, knock-in, mutation, deletion, RNA interference, or other suitable method. Suitable methods for rendering a genomic allele encoding a target protein of interest non-functional are well known to those of skill in the art and the invention is not limited in this respect.

Nucleic acids, for example, nucleic acids encoding a ligand-dependent intein, a hybrid protein, an intein domain, or a ligand-binding domain, as described herein, as well as hybrid proteins comprising an intein inserted into the amino acid sequence of a target protein can be introduced into a target cell by methods well known to those of skill in the art, for example, by contacting a target cell with a nucleic acid encoding a hybrid protein (e.g., transfection, transduction, infection, electroporation), or by contacting a target cell with a hybrid protein fused to a protein transduction domain to effect protein transduction. Such delivery methods are well known in the art and the invention is not limited in this respect.

Methods of Evolving Ligand-Dependent Inteins

In some embodiments, FACS-based screening methods are provided herein that are useful for the directed evolution of inteins for specific applications, e.g., at a specific temperature range, or in a specific cell or tissue type. In some embodiments, these methods use a diversified intein-library, for example, diversified by error-prone PCR as described in detail elsewhere herein, inserted into a target protein that can be detected in a FACS assay, for example, a fluorescent protein, or a cell-surface protein. In some embodiments, intein activity is coupled to an increase in target protein activity, for example, GFP fluorescence. In some embodiments, a diversified library of inteins inserted into a detectable target protein is provided and cells are contacted with this library. Preferably, each cell expresses only one member of the intein library. In some embodiments, the screening method comprises a positive selection, for example, a selection of those cells exhibiting the highest target protein activity upon exposure to an appropriate ligand. In the case of GFP being used as the target protein, cells exhibiting the highest level of GFP fluorescence after exposure to ligand (e.g., 4-HT) are isolated by FACS to obtain a population of cells expressing those members of the intein library with the highest splicing activity. In some embodiments, the screening method further comprises a negative selection. For example, in some embodiments, cells expressing library inteins are subjected to FACS sorting in the absence of ligand. In some embodiments, those cells exhibiting the lowest background target protein activity (e.g., the lowest GFP fluorescence) in the absence of ligand are isolated by FACS to obtain a population of cells with the lowest intein activity in the absence of ligand. The positive and negative selection steps can be combined, in any order, to obtain a population of cells expressing library members with the highest ligand-dependent splicing activity and the lowest splicing background in the absence of ligand. In some embodiments, a positive selection step is followed by a negative selection step. In other embodiments, a negative selection step is followed by a positive selection step. In some embodiments, the population if library inteins or the nucleic acids encoding the library inteins obtained after a positive and a negative selection step are isolated and subjected to an additional round of diversification and selection. FACS selection offers a large dynamic range that can be exploited for the isolation of active and highly active library members, allows analysis of individual library members at the single-cell level, and supports very high-throughput screens; in this work, $\sim 10^7$ cells were screened in a few hours. FACS is also a nondestructive method, and cells collected in this manner are robust enough to be cultured in liquid or on solid media immediately following the screening process, allowing for multiple rounds of selection being conducted on a cell population. Further, the ability to culture and thus amplify the cells resulting from each screen simplifies the process of enriching and isolating desired library members.

Methods of Using Ligand-Dependent Inteins

The ligand-dependent inteins described herein allow for timed modulation of the activity of a target protein of interest in a cell or an organism, both in vitro or in vivo, by addition or administration of an appropriate ligand. Appropriate ligands are well known to those of skill in the art and some of the ligands described herein, for example, tamoxifen and tamoxifen-analogs (e.g., 4-HT) have been proven non-toxic at effective concentrations in clinical trials. Some appropriate ligands described herein are used in the clinic for human therapy, and methods and concentrations for the use of such ligands in vitro, for example, in mammalian cell culture, are well established in the art.

One advantage of the methods described herein is that protein splicing-mediated induction of target protein activity exhibits faster kinetics than modulating transcription or translation of the respective target gene, since the hybrid protein can be activated by intein excision without any time-consuming transcription or translation step involved. Accordingly, ligand-dependent inteins as described herein allow for the study of target proteins in a cell, tissue, organism, or biological pathway without disturbing transcriptional or translational pathways. Since the inteins described herein can be induced with a small molecule independent of their extein context, they are universally applicable, and their use avoids the development of specific inhibitors of each target protein of interest.

In some embodiments, a hybrid protein, which includes a ligand-dependent intein inserted into a target protein, is used to investigate the activity of a protein of interest or the role of a protein of interest in vitro or in vivo. Ligand-dependent inteins provide a means of rapidly activating a protein by the addition of an appropriate ligand, and are thus suitable for investigating biochemical pathways, cell signaling pathways, developmental controls, etc.

A nucleic acid molecule encoding a hybrid protein of a ligand-dependent intein and a target protein as described herein may be transformed into any cell in which the activity of the target protein is to be assessed. For example, for investigating the role of a particular transcription factor in mammalian cells, a nucleic acid molecule encoding a hybrid protein comprising a ligand-dependent intein described herein inserted into the amino acid sequence of the transcription factor can be used to transform mammalian cells. In some embodiments, the mammalian cells do not express the native transcription factor, resulting in the only source of active transcription factor molecules being splice products of the hybrid protein. One of the advantages of the ligand-dependent inteins described herein is that once such an intein or a nucleic acid encoding such an intein is prepared, it may be used in a variety of extein contexts without further manipulation.

In some embodiments, a hybrid protein comprising a ligand-dependent intein described herein is used for therapeutic purposes. In some embodiments, the hybrid protein or a nucleic acid molecule encoding the hybrid protein is administered to a subject or used to transducer or transform cells which are subsequently administered to a subject. In certain embodiments, the hybrid protein is used to treat or prevent a particular disease in a subject. For example, in some embodiments, an appropriate ligand activating the splicing activity of the intein is present only or predominantly in a particular target cell, tissue, or organ of the subject. Accordingly, hybrid protein splicing an, thus, restoration of target protein activity, only or predominantly takes place in that cell, tissue, or organ. In some embodiments, a ligand-dependent intein as described herein may provide temporal control over target protein activity. For example, an appropriate ligand, which activates the splicing activity of the intein, may be provided exogenously or endogenously at a particular time.

In some embodiments, a hybrid protein comprising an intein as described herein embedded in the protein sequence of a target protein of interest is expressed in a cell, tissue, or organism. In some such embodiments, it is desirable to eliminate or diminish expression of the native target protein in the cell, tissue, or organism. This can be achieved by methods well known to those of skill in the art, for example, by gene targeting methods. For example, in some embodiments, the native locus of a gene of interest may be knocked out in a cell, or organism, and a nucleic acid molecule encoding a hybrid protein comprising the target protein and a ligand-dependent intein as described herein may be introduced into the cell or organism to obtain a cell or organism in which only the ligand-inducible, but not the native target protein is expressed.

In some embodiments, a method of using a ligand-dependent intein is provided that involves contacting a target cell with a hybrid protein comprising a ligand-dependent intein or intein domain, as described herein, inserted into the amino acid sequence of a target protein of interest, or with a polynucleotide encoding such a hybrid protein. In some embodiments, a method of using a ligand-dependent intein is provided that involves contacting a cell or tissue comprising or expressing a ligand-dependentintein or intein domain, as described herein, with a ligand binding to the ligand-binding domain of the ligand-dependent intein. In some embodiments, the cell or tissue is contacted with an amount of an appropriate ligand (e.g., 4-HT) that effects self-excision of the ligand-dependent intein from the hybrid protein in at least about 10%, at least about 20%, at least about 30%, at least about 40%, at least about 50%, at least about 60%, at least about 70%, at least about 80%, at least about 90%, at least about 95%, at least about 98%, at least about 99%, or in 100% of the hybrid protein molecules. In some embodiments, a tissue is contacted with an amount of an appropriate ligand (e.g., 4-HT) that effects self-excision of the ligand-dependent intein from the hybrid protein in at least about 10%, at least about 20%, at least about 30%, at least about 40%, at least about 50%, at least about 60%, at least about 70%, at least about 80%, at least about 90%, at least about 95%, at least about 98%, at least about 99%, or in 100% of the cells in the tissue. In some embodiments, the cell or tissue is contacted with an amount of an appropriate ligand (e.g., 4-HT) that restores an activity of the target protein to at least 10%, at least about 20%, at least about 30%, at least about 40%, at least about 50%, at least about 60%, at least about 70%, at least about 80%, at least about 90%, at least about 95%, at least about 98%, at least about 99%, or to at least about 100% of the level of the target protein activity measured or expected in a cell or tissue expressing the native target protein at a similar level as the level of expression of the hybrid protein in the target cell or tissue. Methods of contacting a cell or tissue in vitro or in vivo with an appropriate ligand and for measuring self-excision efficiency, levels of hybrid protein, and/or of mature, spliced target protein, as well as method for measuring the level or target protein activity, are described herein. Additional suitable methods will be apparent to those of skill in the art and the invention is not limited in this respect. Suitable methods for determining target protein activity will, of course depend on the nature of the target protein and the activity to be measured. Methods for measuring a variety of target protein activities (e.g., enzymatic, fluorescent, structural, etc.) are well known to those of skill in the art and the invention is not limited in this respect.

In some embodiments, a method of using a ligand-dependent intein is provided that involves generating an organism, for example, a transgenic organism, expressing a hybrid protein comprising a ligand-dependent intein or intein domain, as described herein, inserted into the amino acid sequence of a target protein of interest, in at least one cell. In some embodiments, a method of using a ligand-dependent intein is provided that involves administering to the organism comprising or expressing a ligand-dependent intein or intein domain, as described herein, a ligand binding to the ligand-binding domain of the ligand-dependent intein. In some embodiments, an amount of an appropriate ligand (e.g., 4-HT) is administered that effects self-excision of the ligand-dependent intein from the hybrid protein in at least about 10%, at least about 20%, at least about 30%, at least about 40%, at least about 50%, at least about 60%, at least about 70%, at least about 80%, at least about 90%, at least about 95%, at least about 98%, at least about 99%, or in 100% of the hybrid protein molecules. In some embodiments, an amount of an appropriate ligand (e.g., 4-HT) is administered that effects self-excision of the ligand-dependent intein from the hybrid protein in at least about 10%, at least about 20%, at least about 30%, at least about 40%, at least about 50%, at least about 60%, at least about 70%, at least about 80%, at least about 90%, at least about 95%, at least about 98%, at least about 99%, or in 100% of a cell population, for example, of a cell population in a tissue of interest comprised in the organism. In some embodiments, an amount of an appropriate ligand (e.g., 4-HT) is administered to the organism that restores an activity of the target protein to at least 10%, at least about 20%, at least about 30%, at least about 40%, at least about 50%, at least about 60%, at least about 70%, at least about 80%, at least about 90%, at least about 95%, at least about 98%, at least about 99%, or to about 100% of the level of the target protein activity measured or expected in a cell, tissue, or organism expressing the native target protein at a similar level as the level of expression of the hybrid protein.

In some embodiments, a method is provided that includes ligand-dependent hybrid protein splicing in a cell, tissue, or organism that is diseased or serves as a disease model. In some such embodiments, the target protein comprised in the hybrid protein exhibits a therapeutic function upon excision of the ligand-dependent intein from the hybrid protein.

In some embodiments, a method of using an intein described herein is provided that includes the generation of a hybrid protein comprising a mitochondrial target protein and an intein or intein domain as described herein embedded into the target protein sequence. In some embodiments, the target protein is a highly hydrophobic protein. In some embodiments, the hybrid protein is less hydrophobic than the target protein, based on the embedded intein or intein domain, allowing for delivery of the hybrid protein to the target organelle and the restoration of target protein hydrophobicity and/or other activity in the target organelle (e.g., a mitochondrion).

Additional applications of the ligand-dependent inteins and intein domains described herein will be apparent to those of skill in the art. The inteins provided herein can be used for any application that conventional inteins are useful for (e.g., as described in International PCT Patent Application Serial Number PCT/US2005/010805, filed Mar. 30, 2005; U.S. Pat. No. 7,192,739, issued Mar. 20, 2007; U.S. Pat. No. 7,541,450, issued Jun. 2, 2009; and on pages 1-10, 193-207, 211-229, 233-252, and 325-341 of Gross, Belfort, Derbyshire, Stoddard, and Wood (Eds.) *Homing Endonucleases and Inteins* Springer Verlag Heidelberg, ISBN 9783540251064; the contents of each of which are incorporated herein by reference).

However, the inteins and intein domains provided herein have the advantage of optimized efficiency within a temperature range of about 30° C. to about 37° C., making them an attractive tool for applications in mammalian cells.

The function and advantage of these and other embodiments of the present invention will be more fully understood from the example section below. The following examples are intended to illustrate the benefits of the present invention and to describe particular embodiments, but do neither exemplify nor limit the full scope of the invention.

Kits

Some embodiments of this invention provide kits comprising an intein, intein domain, ligand-dependent domain, or hybrid protein as described herein. In some embodiments, a kit is provided that comprises a nucleic acid molecule encoding an intein, intein domain, ligand-dependent domain, or hybrid protein as described herein. For example, in some kits, a nucleic acid or a plurality of nucleic acids may be provided that allow efficient generation of hybrid proteins via restriction or recombination cloning. For example, some kits may comprise a nucleic acid molecule comprising a sequence encoding a ligand-dependent intein as provided herein (e.g., as provided in SEQ ID NOs 3-8), wherein the intein-encoding sequence is flanked by multiple cloning sites allowing in-frame cloning of target protein-encoding sequences, target protein (N) and target protein (C), upstream and downstream of the intein-encoding sequence, respectively. In some embodiments, the intein-encoding sequence is comprised in a vector, for example, a bacterial plasmid vector, that comprises an origin of replication allowing for efficient replication and propagation in a bacterial host. In some embodiments, the vector further comprises a mammalian promoter driving expression of the intein-encoding sequence and any adjacent target protein-encoding sequences, in mammalian cells. In some embodiments, the vector further comprises a transcriptional termination signal or a transcriptional insulator downstream of the intein-encoding sequence and any adjacent target protein-encoding sequence or cloning site.

In some embodiments, the kit comprises a container and/or accompanying instructions or specifications for the use of the included inteins or intein-encoding. The kit may also include other polynucleotides, vectors, cells, buffers, enzymes, nucleotides, tubes, plates, ligand, maps, sequences, etc. that are useful in connection with the ligand-dependent inteins or intein encoding nucleic acids described herein.

EXAMPLES

Materials and Methods

Yeast Strains and Media

Media consisted of yeast nitrogen base (Sigma), 4% dextrose, and synthetic drop out supplements lacking uracil (MP Biomedical). Yeast were cultured in liquid medium or on agar plates at 30° C. The yeast strain RDY98 (Erg6del::TRP1 pdr1del::KanMX pdr3::HIS3 ade2-1 trp1-1 his3-11,15 ura3-52 leu2-3,112 can1-100) was provided by Professor Allen Buskirk at Brigham Young University. Protein induction was performed in media consisting of yeast nitrogen base (Sigma), 4% galactose, 4% raffinose, 0.4% dextrose, synthetic drop out supplements lacking uracil (MP Biomedical), and 1% of 100× penicillin-streptomycin solution (Cellgro) at 30° C.

Mammalian Cell Culture

HEK293 cells were cultured in Dulbecco's modified Eagle medium (DMEM):F12 medium with 10% fetal bovine serum (FBS) and 1% of 100× penicillin-streptomycin solution (Cellgro) according to standard protocols. Transient transfections were performed using Effectene (Qiagen) following the manufacturer's protocol.

Library Construction

Error-prone PCR was carried out using 2-4 and 3-2 intein sequences as templates using DNA bases 8-oxo-2'-deoxyguanosine (8-oxo-dGTP) and 6-(2-deoxy-b-D-ribofuranosyl)-3,4-dihydro-8Hpyrimido-[4,5-C][1,2]oxazin-7-one (dPTP) purchased from TriLink BioTechnologies as previously described (Zaccolo et al., 1996) using oligonucleotides 5'-TAT GTA CAG GAA CGC ACT ATA TCT TTC AAA GAT GAC GGG AAC TAC GCA TGC-3' (SEQ ID NO: 14) and 5'-GTG CAC GAC AAC CCC TTC GGC GAC GAG GGT GTG CAG TTC CTC GAC CTC GAG-3' (SEQ ID NO: 15). Mutagenized intein PCR products were inserted into p416Gal1 GFP-intein vector pre-cut with SphI and XhoI (to remove the existing intein sequence) by in vivo homologous recombination of overlapping PCR fragments as previously described (Raymond et al., 1999).

Plasmid Construction

GFP-intein library members were amplified by PCR from the corresponding p416Gal1 library vector using oligonucleotides 5'-CTC GTT TAGTGA ACC GTC AGA GCC GCC ATG GCA AGC AAA GGA GAA-3' (SEQ ID NO: 16) and 5'-CTA CTT GTC ATC GTC GTC CTT GTA ATC TTT GTA GAG CTC ATC CAT-3' (SEQ ID NO: 17). pFLAG-CMV-5.1 (Sigma) was amplified by PCR using oligonucleotides 5'-ACA CAT GGC ATG GAT GAG CTC TAC AAA GAT TAC AAG GAC GAC GAT-3' (SEQ ID NO: 18) and 5'-TTC TTC TCC TTT GCT TGC CAT GGC GGCTCT GAC GGT-TCA CTA AAC-3' (SEQ ID NO: 19). The PCR products were ligated together through isothermal assembly (Gibson et al., 2009). The resulting ligated vectors were purified using MinElute columns (Qiagen) and eluted with 10 µL deionized water. 1 µL of this elution was transformed into NEB Turbo chemically competent E. coli cells (New England Biolabs) and plated onto LB+carbenicillin agar plates. Plates were incubated overnight at 37° C., and individual colonies were picked and sequenced to verify correct plasmid construction.

p3XFlag-CMV-14 (Sigma) vectors with Gli1-intein (2-4 and 3-2), and Gli3T-intein (2-4 and 3-2) sequences were previously described (Yuen et al., 2006). p3XFlag-CMV-14 mCherry-intein (2-4 and 3-2) vectors were constructed by cloning the 2-4 and 3-2 intein sequences into the pRSET-B mCherry vector provided by Professor Roger Tsien (University of California at San Diego). The mCherry-intein 2-4 and mCherry-intein 3-2 sequences were then amplified using oligonucleotides introducing a 5' EcoRI site and a 3' BamHI site and ligated into EcoRI- and BamHI-digested p3XFlag-CMV-14 vector. 30R3-1 intein sequence and 37R3-2 intein sequence were amplified using the following oligonucleotides compatible with mCherry, Gli1, or Gli3 contexts.

mCherry: 5'-TTC GAG GAC GGC GGC GTG GTG ACC GTG TGC CTT GCC GAG GGT ACC-3' (SEQ ID NO: 20) and 5'-GCC GTC CTG CAG GGA GGA GTC CTG GCA GTT GTG CAC GAC AAC CCC-3' (SEQ ID NO: 21). Gli1: 5'-ATC CAC GGG GAG CGG AAG GAA TTC GTG TGC CTT GCC GAG GGT ACC-3' (SEQ ID NO: 22) and 5'-CTC CCT CGA GCA ACC TCC CCA ATG GCA GTT GTG CAC GAC AAC CCC-3' (SEQ ID NO: 23). Gli3: 5'-ATT CAT GGA GAA AAG AAG GAA TTC GTG TGC CTT GCC GAG GGT ACC-3' (SEQ ID NO: 24) and 5'-CTC TCG AGA ACA ATC AAG CCA GCG GCA GTT GTG CAC GAC AAC CCC-3' (SEQ ID NO: 25). The p3XFlag-pCMV-14 vector was amplified using oligonucleotides 5'-CTC GTC GCC GAA GGG GTT GTC-3' (SEQ ID NO: 26) and 5'-ATC GAA GAT TCG GGT ACC CTC-3' (SEQ ID NO: 27). The intein PCR products and the vector PCR product were ligated together through the isothermal assembly method (Gibson et al., 2009) and the resulting ligated material was treated as discussed above.

FACS Screening and Analysis

Yeast cells transformed with library plasmids were cultured for 24 hrs in the appropriate synthetic drop out media in 30° C. Cells were washed and resuspended in protein induction media and cultured for another 24 hrs at 30° C. After 24 hrs of protein induction, cells were treated with 1 µM 4-HT or left untreated with 4-HT as appropriate for the prescribed amount of time in either 30° C. or 37° C. After the appropriate length of time, cells were harvested by washing once in PBS, then resuspended in PBS with 0.1% bovine serum albumin (BSA) (Sigma). Cell sorting was performed using a MoFlo cell sorter (DakoCytomation). Cell fluorescence analysis was carried out on a BD LSRII cell analyzer.

HEK293 cells were grown in 10 cm dishes or 6-well plates and transfected with relevant mammalian vectors using Effectene. After growth in the absence of 4-HT or in the presence of 1 µM 4-HT for 24 hours, cells were trypsinized and resuspended in 500 µL of phosphate buffered saline with 1% FBS and 75 U/mL DNase (New England Biolabs). Cell fluorescence analysis was carried out on a BD LSRII cell analyzer.

Western Blots

Western blots were performed using Nu-PAGE 12% Bis-Tris gels (Invitrogen) in 3-(Nmorpholino) propanesulfonic acid (MOPS)-sodium dodecyl sulfate (SDS) buffer (Invitrogen). SDSpolyacrylamide gel electrophoresis (PAGE) and Western blotting were performed using standard protocols. Gels were transferred onto polyvinylidene fluoride (PDVF) membranes (Millipore). Western blots were processed using a mouse anti-FLAG antibody (Sigma) as the primary antibody and a secondary Alexa Fluor 800-conjugated goat anti-mouse antibody (Li-cor Biosciences), then visualized and quantitated using an Odyssey imager (Li-cor Biosciences).

Reversion Mutant Construction

Each evolved amino acid change was the result of a single nucleotide mutation. Each reversion mutant was generated using the QuikChange method (Stratagene) with Pfu Turbo and the following oligonucleotides (the mutated base pair is underlined in each oligonucleotide pair).

A34V:

(SEQ ID NO: 28)
5'-CGC AAG CCT ATT CAT GTC GTG GCT GTT GCC AAG GAC GGA ACG CTG CTC GCG-3'
and (SEQ ID NO: 29)
5'-CGC GAG CAG CGT TCC GTC CTT GGC AAC AGC CAC GAC ATG AAT AGG CTT GCG-3'.

T66I:
(SEQ ID NO: 30)
5'- GGG TTG CGG ATC GCC GGT GGC GCC ATC GTG TGG GCG ACA CCC GAT CAC AAG-3' and (SEQ ID NO: 31)
5'- CTT GTG ATC GGG TGT CGC CCA CAC GAT GGC GCC ACC GGC GAT CCG CAA CCC-3'.

P124L:
(SEQ ID NO: 32)
5'- TTG TTG GAT GCT GAG CCC CCC ATA CTC TAT TCC GAG TAT GAT CCT ACC AGT-3' and (SEQ ID NO: 33)
5'- ACT GGT AGG ATC ATA CTC GGA ATA GAG TAT GGG GGG CTC AGC ATC CAA CAA-3'.

C178R:
(SEQ ID NO: 34)
5'-CCA TGA TCA GGC CCA CCT TCT AGA ACG TGC CTG GCT AGA GAT CCT GAT GAT-3'.

and (SEQ ID NO: 35)
5'- ATC ATC AGG ATC TCT AGC CAG GCA CGT TCT AGA AGG TGG GCC TGA TCA TGG-3'.

K328T:
(SEQ ID NO: 36)
5'- GAG CAT CTG TAC AGC ATG AAG TAC ACG AAC GTG GTG CCC CTC TAT GAC CTG-3' and (SEQ ID NO: 37)
5'- CAG GTC ATA GAG GGG CAC CAC GTT CGT GTA CTT CAT GCT GTA CAG ATG CTC-3'.

G375E:
(SEQ ID NO: 38)
5'- TTC CTG CAC GAC ATG CTG GCG GAA GAA CTC CGC TAT TCC GTG ATC CGA GAA-3' and (SEQ ID NO: 39)
5'- TTC TCG GAT CAC GGA ATA GCG GAG TTC TTC GCC CAG CAT GTC GTG CAG GAA-3'.

Results

Evolution Scheme for Improved 4-HT-Dependent Inteins

To improve the splicing characteristics of the evolved 4-HT dependent inteins, the high-throughput fluorescence-activated cell sorting (FACS) screen previously used to isolate active and inactive inteins from mixed starting populations (Buskirk et al., 2004) was modified (FIG. 1A). The 4-HT-dependent intein was genetically inserted in place of Cys 108 of GFP(uv), a FACS-optimized GFP mutant, which places the intein near the mid-point of a β-strand and abolishes fluorescence until splicing takes place (Ormo et al., 1996; Buskirk et al., 2004). During positive screens for intein splicing activity, cells that exhibited GFP fluorescence in the presence of 4-HT were collected, while during negative screens cells that remained non-fluorescent in the absence of 4-HT were collected (FIG. 1B). Using error-prone PCR with mutagenic dNTPs (Zaccolo et al., 1996), point mutations were randomly introduced into the genes of the two best inteins (including the ligand-binding domain) resulting from a previous intein evolution effort, the 2-4 and 3-2 inteins (described in detail in International Patent Application Serial Number PCT/US2005/010805, filed Mar. 30, 2005; U.S. Pat. No. 7,192,739, filed Mar. 30, 2005; and U.S. Pat. No. 7,541,450, filed Mar. 19, 2007; the entire contents of each of which are incorporated by reference herein). The resulting intein gene library was cloned into the p416Gal1 vector in *S. cerevisiae* RDY98 using gap repair homologous recombination (Raymond et al., 1999) to obtain a starting library size of $7 \times 10_6$ clones. This starting library was subjected to two evolution efforts in parallel, one conducted at 30° C. and one at 37° C. (FIG. 1C).

Each round of evolution consisted of at least two positive screens and one negative screen (FIG. 1B). Positive screen 1

(P1) for each round collected the 5% most fluorescent library members in the presence of 4-HT. The second positive screen (P2) in each round collected library members that exhibited better splicing activity than the parental 3-2 intein in the presence of 4-HT by collecting the cells that were more fluorescent than cells transformed with a 3-2 intein-GFP construct. In Round 2, a third positive screen was carried out (P3) that further enriched for library members with better splicing activity than the 3-2 intein in the presence of 4-HT. As the final screening step in each round of evolution, a single negative screen (N) collected library members that did not generate spliced GFP (i.e., were not fluorescent) in the absence of 4-HT. Surviving gene pools were diversified after each round. Following Round 1, the genes of the surviving library members in each of the two libraries were separately mutagenized using error-prone PCR before re-cloning into yeast as the starting library for Round 2. After Round 2, surviving genes from the 30° C. and 37° C. screens were combined and subjected to in vitro homologous recombination using the StEP method (Zhao and Zha, 2006). The resulting recombined library was subjected to separate Round 3 screens at 30° C. and at 37° C. Overall, the entire evolution process comprised three complete rounds containing 10 individual screening steps each for the 30° C. and the 37° C. efforts (FIG. 1C).

Splicing Characteristics of Evolved Inteins

Clones from the 30° C. and the 37° C. libraries surviving each of the rounds of evolution were isolated and the genes encoding their inteins were sequenced. Three sequences each from the 30° C. and 37° C. libraries following Round 3 were selected for detailed characterization on the basis of their high degree of abundance in the final evolved pools. These six intein sequences are summarized in Table 1. The newly evolved clones are designated 30RX-Y (from evolution at 30° C.) or 37RX-Y (from evolution at 37° C.), where X refers to the round number from which the clone was isolated and Y refers to the clone number within that round. Mutations Val34Ala, Ile66Thr, Thr328Lys, and Glu375Gly are shared among clones in both the 30° C. and 37° C. libraries. Leu124Pro was observed only in the 30° C. library, and Asp129Asn and Cys178Arg are only observed in the 37° C. library.

of the human estrogen receptor and comprise the ligand-binding domain of these ligand-dependent inteins.

2-4 intein:
(SEQ ID NO: 1)
CLAEGTRIFDPVTGTTHRIEDVVDGRKPIHVVAAAKDGTLLARPVVSWFD

QGTRDVIGLRIAGGAIVWATPDHKVLTEYGWRAAGELRKGDRVA*GPGGSG*

NSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKYKNVVPLYDLLLEMLDAHRLHAGG

*SGAS*RVQAFADALDDKFLHDMLAEELRYSVIREVLPTRRARTFDLEVEEL

HTLVAEGVVVHNC 3-2 intein:
(SEQ ID NO: 2)
CLAEGTRIFDPVTGTTHRIEDVVDGRKPIEVVAVAKDGTLLARPVVSWFD

QGTRDVIGLRIAGGAIVWATPDHKVLTEYGWRAAGELRKGDRVA*GPGGSG*

NSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKYTNVVPLYDLLLEMLDAHRLHAGG

*SGAS*RVQAFADALDDKFLHDMLAEELRYSVIREVLPTRRARTFDLEVEEL

HTLVAEGVVVHNC

The amino acid sequences of six evolved inteins are provided below. Amino acid changes relative to the 3-2 parent intein are underlined.

TABLE 1

Mutations isolated in evolved inteins. Three clones each from the 30° C. and 37° C. evolution efforts were chosen based on their abundance among DNA sequences surviving Round 3. The mutations compared with the 3-2 intein sequence are shown. Val34Ala, Ile66Thr, and Glu375Gly are mutations in the intein, whereas Leu124Pro, Asp129Asn, Cys178Arg, and Thr328Lys are mutations in the ligand-binding domain.

| evolved intein clone | intein mutations | | ligand-binding domain mutations | | | intein mutation | |
|---|---|---|---|---|---|---|---|
| 30R3-1 | Val34Ala | Ile66Thr | Leu124Pro | | | Thr328Lys | Glu375Gly |
| 30R3-2 | Val34Ala | Ile66Thr | | | | Thr328Lys | |
| 30R3-3 | Val34Ala | Ile66Thr | Leu124Pro | | | Thr328Lys | |
| 37R3-1 | Val34Ala | Ile66Thr | | Asp129Asn | Cys178Arg | Thr328Lys | Glu375Gly |
| 37R3-2 | Val34Ala | Ile66Thr | | | Cys178Arg | Thr328Lys | |
| 37R3-3 | | Ile66Thr | | | Cys178Arg | Thr328Lys | |

Amino acid sequences of inteins 2-4, and 3-2 are given below. The final amino acid in each of these sequences is an appended cysteine, often referred to as the first amino acid of the C-terminal extein in the literature. Bold and underlined residues constitute the N-terminal and C-terminal intein domains, derived from residues 1-94 and 383-440 of RecA, respectively. The two 6 amino acid linkers are in italics. The bold residues in the center are derived from residues 304-551

30R3-1 intein:
(SEQ ID NO: 3)
CLAEGTRIFDPVTGTTHRIEDVVDGRKPIHVVA_A_AKDGTLLARPVVSWFD

QGTRDVIGLRIAGGA_T_VWATPDHKVLTEYGWRAAGELRKGDRVAGPGGSG

NSLALSLTADQMVSALLDAEPPI_P_YSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKY<u>K</u>NVVPLYDLLLEMLDAHRLHAGG

SGASRVQAFADALDDKFLHDMLAE<u>G</u>LRYSVIREVLPTRRARTFDLEVEEL

HTLVAEGVVVHNC

30R3-2 intein:
(SEQ ID NO: 4)
CLAEGTRIFDPVTGTTHRIEDVVDGRKPIHVVA<u>A</u>AKDGTLLARPVVSWFD QGTRDVIGLRIAGGA<u>T</u>VWATPDHKVLTEYGWRAAGELRKGDRVAGPGGSG

NSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKY<u>K</u>NVVPLYDLLLEMLDAHRLHAGG

SGASRVQAFADALDDKFLHDMLAEELRYSVIREVLPTRRARTFDLEVEEL

HTLVAEGVVVHNC

30R3-3 intein:
(SEQ ID NO: 5)
CLAEGTRIFDPVTGTTHRIEDVVDGRKPIHVVA<u>A</u>AKDGTLLARPVVSWFD QGTRDVIGLRIAGGA<u>T</u>VWATPDHKVLTEYGWRAAGELRKGDRVAGPGGSG NSLALSLTADQMVSALLDAEPPI<u>P</u>YSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKY<u>K</u>NVVPLYDLLLEMLDAHRLHAGG

SGASRVQAFADALDDKFLHDMLAEELRYSVIREVLPTRRARTFDLEVEEL

HTLVAEGVVVHNC

37R3-1 intein:
(SEQ ID NO: 6)
CLAEGTRIFDPVTGTTHRIEDVVDGRKPIHVVA<u>A</u>AKDGTLLARPVVSWFD QGTRDVIGLRIAGGA<u>T</u>VWATPDHKVLTEYGWRAAGELRKGDRVAGPGGSG NSLALSLTADQMVSALLDAEPPILYSEY<u>N</u>PTSPFSEASMMGLLTNLADRE LVHMINWAKRVPGFVDLTLHDQAHLLE<u>R</u>AWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKY<u>K</u>NVVPLYDLLLEMLDAHRLHAGG

SGASRVQAFADALDDKFLHDMLAE<u>G</u>LRYSVIREVLPTRRARTFDLEVEEL

HTLVAEGVVVHNC

37R3-2 intein:
(SEQ ID NO: 7)
CLAEGTRIFDPVTGTTHRIEDVVDGRKPIHVVA<u>A</u>AKDGTLLARPVVSWFD QGTRDVIGLRIAGGA<u>T</u>VWATPDHKVLTEYGWRAAGELRKGDRVAGPGGSG

NSLALSLTADQMVSALLDAEPPILYSEYDPTSPFSEASMMGLLTNLADRE

LVHMINWAKRVPGFVDLTLHDQAHLLE<u>R</u>AWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKY<u>K</u>NVVPLYDLLLEMLDAHRLHAGG

SGASRVQAFADALDDKFLHDMLAEELRYSVIREVLPTRRARTFDLEVEEL

HTLVAEGVVVHNC

37R3-3 intein:
(SEQ ID NO: 8)
CLAEGTRIFDPVTGTTHRIEDVVDGRKPIHVVAVAKDGTLLARPVVSWFD QGTRDVIGLRIAGGA<u>T</u>VWATPDHKVLTEYGWRAAGELRKGDRVAGPGGSG

NSLALSLTADQMVSALLDAEPPILYSEYDPTSPFSEASMMGLLTNLADRE

LVHMINWAKRVPGFVDLTLHDQAHLLE<u>R</u>AWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKY<u>K</u>NVVPLYDLLLEMLDAHRLHAGG

SGASRVQAFADALDDKFLHDMLAEELRYSVIREVLPTRRARTFDLEVEEL

HTLVAEGVVVHNC

Figure 6:
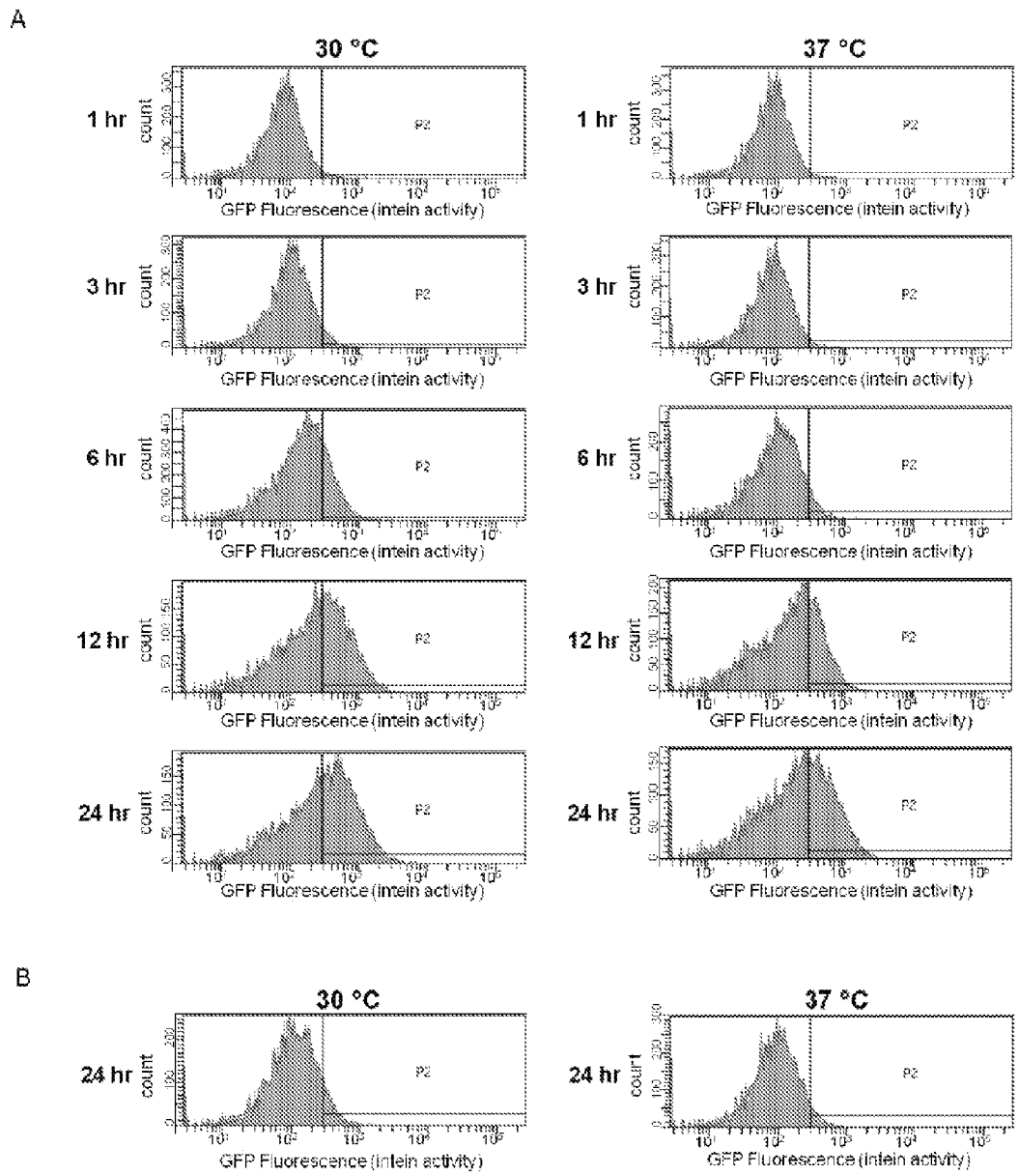
FIG. 6. Characterization of newly evolved inteins in yeast cells by flow cytometry. The P2 analysis gate indicates the cell population that is positive for GFP fluorescence. (A) Representative FACS plots of cells transformed with 30R3-1 intein (SEQ ID NO: 3) in the GFP context treated with 1 μM 4-HT for the durations shown at 30° C. and 37° C. The increase in cell fluorescence over time indicates an accumulation of functional, spliced GFP in cells treated with 4-HT. (B) Representative FACS plots of cells transformed with 30R3-1 intein (SEQ ID NO: 3) in the GFP context without 4-HT, incubated for 24 h. The lack of significant increase in the fluorescent population over the course of 24 h indicates low levels of background splicing.

All six evolved inteins were assayed for splicing function in the GFP context in yeast cells at both 37° C. and 30° C., and their activities were compared with those of the original 2-4 and 3-2 inteins under the same conditions. A FLAG-tag was appended at the C-terminal end of the GFP-intein sequence to facilitate detection of both the spliced and unspliced protein products. Cells treated with 1 μM 4-HT or without 4-HT at time points from 1 hour to 24 hours were subjected to FACS analysis (FIG. 6), and the spliced and unspliced proteins in the corresponding cell lysates were quantified by Western blot (FIG. 2A) and densitometry. The percentage of spliced protein was calculated as the amount of spliced protein divided by the total amount of spliced+unspliced protein for each sample.

Figure 2:
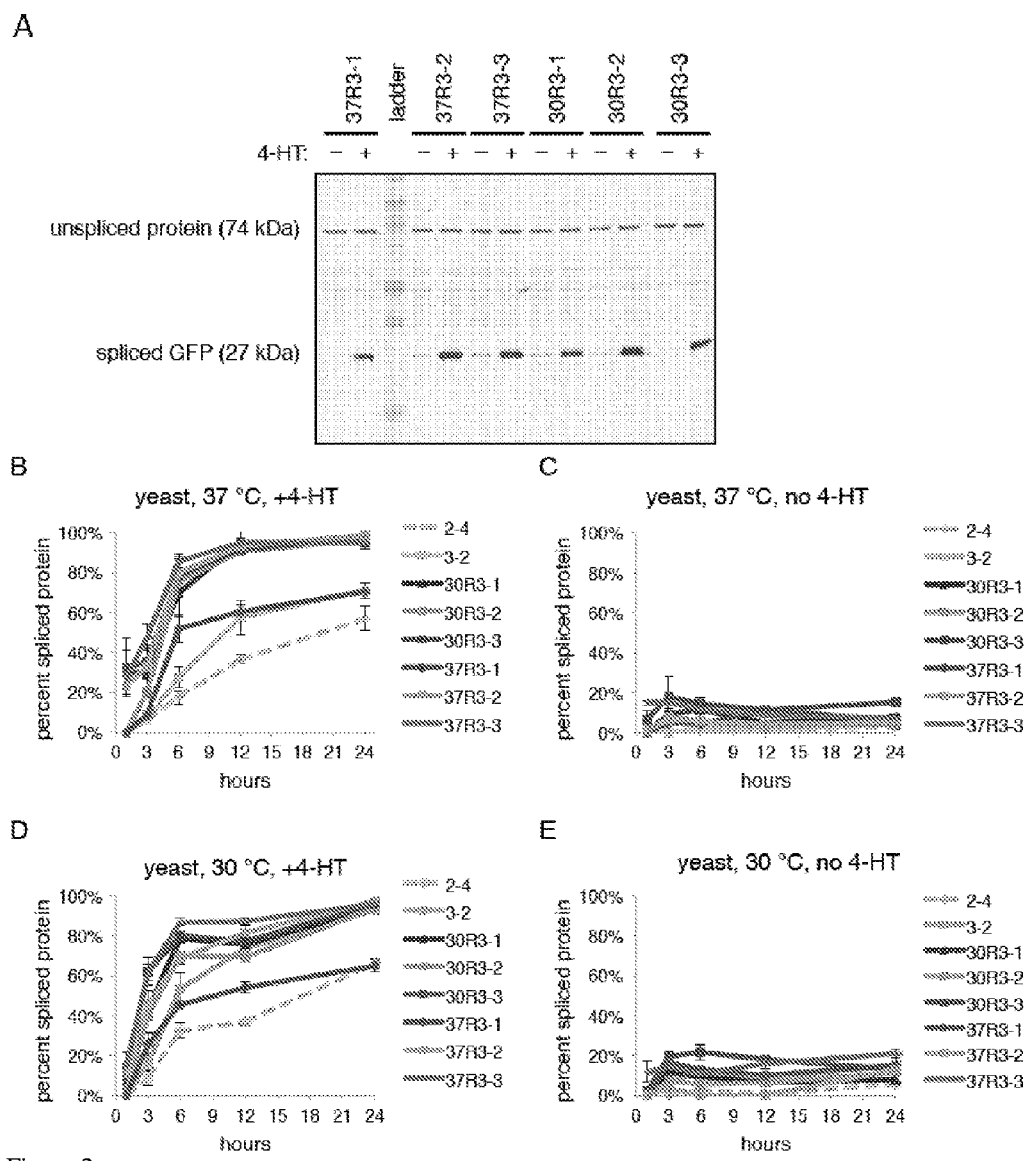
FIG. 2. Characterization of newly evolved inteins in yeast cells. (A) Representative Western blot of lysates from yeast cells expressing evolved intein variants in the context of Green Fluorescent Protein (GFP). Each lane shows lysate from $2.5 \times 10^6$ cells after six hours of growth at 30° C. in the absence or presence of 1 μM 4-HT visualized with an anti-FLAG-tag antibody. Quantitation of spliced and unspliced protein bands by densitometry was used to calculate the percent spliced protein shown in the rest of the figure. (B)-(E) Intein splicing characteristics in yeast at various time points in the context of GFP at 30° C. ((D) and (E)) or 37° C. ((B) and (C)), either with ((B) and (D)) or without ((C) and (E)) 1 μM 4-HT. Error bars represent the standard deviation of at least three independent experiments.

In yeast cells at 37° C., all six newly evolved inteins exhibit substantially faster production of spliced proteins as well as a significantly higher percentage of spliced product in the presence of 4-HT as compared to the parental 2-4 and 3-2 inteins (FIG. 2B). Compared to the original 2-4 or 3-2 inteins, the most active inteins at 37° C. generate up to 8-fold more spliced protein 3 hours after 4-HT addition and up to 5-fold more spliced protein at 6 hours after 4-HT addition (FIG. 2B). For example, while the 2-4 and 3-2 inteins generated 17-27% spliced GFP after 6 hours at 37° C., the six newly evolved inteins resulted in 70-86% spliced GFP at the same time point. Likewise, while the 2-4 and 3-2 inteins did not generate significant amounts of spliced protein 1 hour after 4-HT treatment, the newly evolved inteins produced 25-35% spliced protein at this early time point. For five of the six clones (all but clone 30R3-3); splicing in the absence of 4-HT remained low (typically <10% after 24 hours; see FIG. 2C). Total protein expression per yeast cell of all six inteins at each time point were within 10% of the expression levels observed with the 3-2 intein (unpublished data), suggesting that the newly evolved inteins do not alter protein expression levels compared with the 3-2 intein and are not unusually susceptible to degradation.

In yeast cells grown at 30° C., five of the six newly evolved inteins (all but clone 37R3-1) exhibit more efficient splicing by the six-hour time point compared to the 2-4 and 3-2 inteins (FIG. 2D). Splicing in the absence of 4-HT after 24 hours was generally ≤15%, the level of background splicing observed for the 3-2 intein after 24 hours (FIG. 2E). The newly evolved inteins generated 3.6- to 7-fold higher levels of spliced protein at 3 hours, and 1.6- to 2.6-fold higher levels of spliced protein at 6 hours, relative to the 3-2 or 2-4 inteins, respectively. At later time points (12 or 24 hours) splicing efficiencies for the newly evolved inteins excluding 37R3-1 were generally high (≥70%), similar to that of the 3-2 intein. As observed in the 37° C. assays, the protein expression levels per yeast cell of each intein were within ±10% of the level observed with the 3-2 intein at each of the time points. Taking into consideration splicing rate, overall splicing efficiency in the presence of 4-HT, and background splicing in the absence of 4-HT, the best performing evolved intein clone for use at 37° C. was 37R3-2, and the best clone at 30° C. was 30R3-1. Together, these results indicate that the evolution strategy described above resulted in inteins with substantially improved splicing speed and yields of spliced protein in yeast at 30° C. and especially at 37° C., without significantly impairing 4-HT dependence.

Ligand-Dependent Splicing of Newly Evolved Inteins in Mammalian Cells

Figure 3:
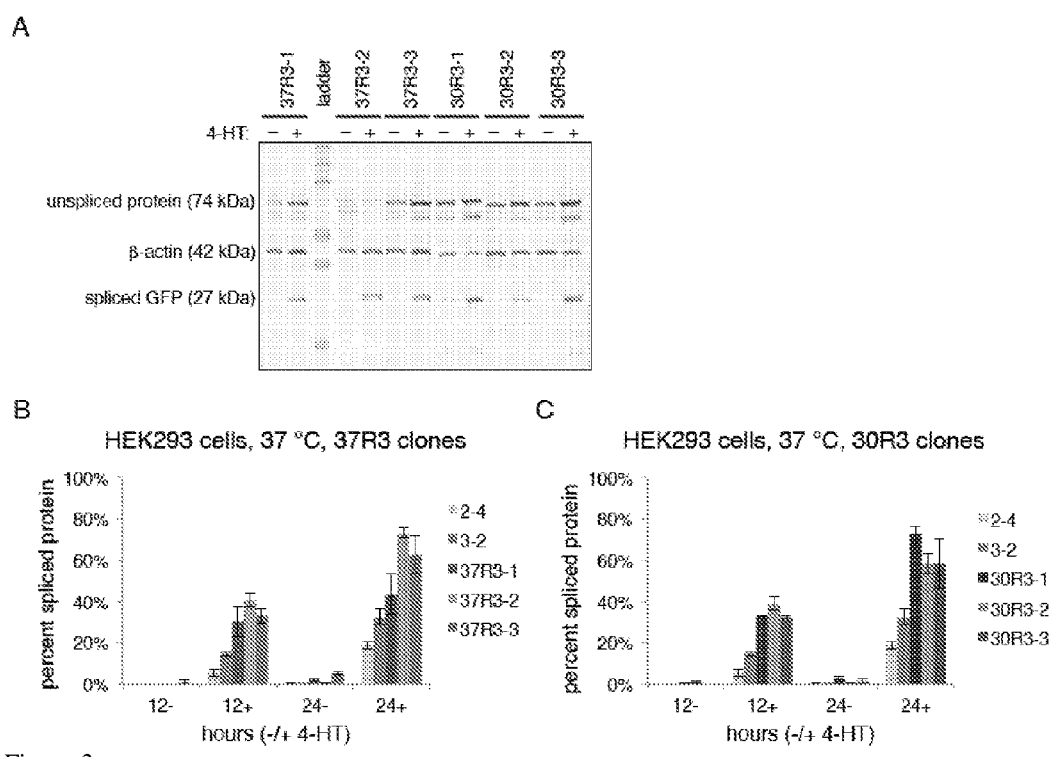
FIG. 3. Characterization of newly evolved inteins in mammalian cells. (A) Representative Western blot of lysates from HEK293 cells, a human embryonic kidney-derived cell line, expressing evolved intein variants in the context of GFP. Each lane shows lysate from cells after 12 hours of growth at 37° C. in the absence or presence of 1 μM 4-HT processed with an anti-FLAG-tag antibody to visualize spliced and unspliced GFP, and an anti-β-actin antibody to visualize β-actin, which served as a loading control. Quantitation of spliced and unspliced protein bands by densitometry was used to calculate the percent spliced protein shown in the rest of the figure. (B) and (C) Splicing characteristics of inteins in the GFP context in HEK293 cells at 37° C. after 12 and 24 hours incubation in the presence or absence of 1 μM 4-HT. Three evolved inteins from the 37° C. evolution effort are shown in (B), and three evolved inteins from the 30° C. evolution effort are shown in (C). Error bars represent the standard deviation of at least three independent experiments.
Figure 7:
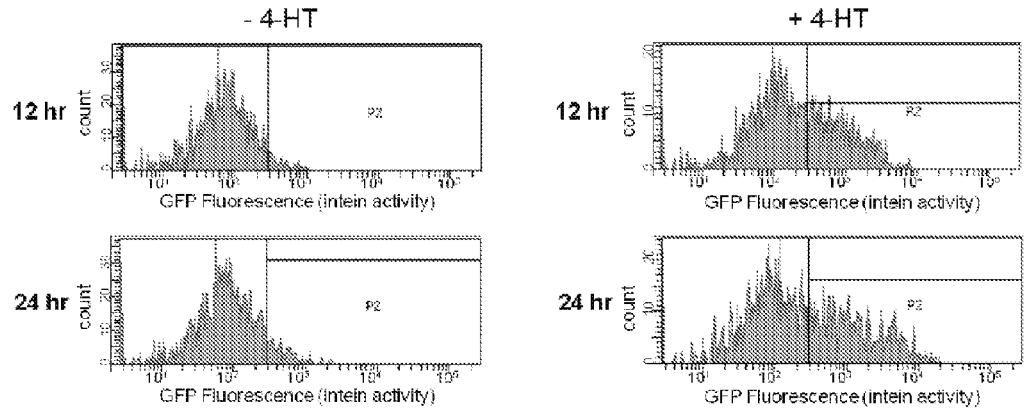
FIG. 7. Characterization of newly evolved inteins in mammalian cells by flow cytometry. Representative FACS plots of HEK293 cells transfected with DNA expressing the 37R3-2 intein in the GFP context without 4-HT or treated with 1 μM 4-HT for 12 h or 24 h at 37° C. are shown.

All six evolved intein sequences described above in the GFP context were cloned into a pCMV promoter-based mammalian expression vector with a C-terminal FLAG-tag for Western blot analysis. HEK293 cells were transfected with these vectors, incubated for 24 hours at 37° C., then treated with Dulbecco's modified Eagle medium (DMEM):F12 with 10% fetal bovine serum (FBS) containing 1 µM final concentration of 4-HT or with the same medium lacking 4-HT. The cells were incubated at 37° C. for an additional 12-24 hours then harvested for FACS (FIG. 7) and Western blot analyses (FIG. 3A). Consistent with the characteristics of the newly evolved inteins in yeast cells, the three assayed clones evolved at 37° C. all exhibit faster GFP splicing kinetics and higher overall splicing yields at both the 12-hour and 24-hour time points compared with the 2-4 or 3-2 inteins (FIG. 3B). The best 37° C. clone, 37R3-2, exhibited 3.8-fold and 2.2-fold higher GFP splicing efficiency after 24 hours than the original 2-4 and 3-2 intein, respectively (73% spliced GFP for 37R3-2 vs. 19% for 2-4 and 33% for 3-2). Background splicing in the absence of 4-HT was not observed for 37R3-2 (FIG. 3B), further consistent with the high ratio of ligand-induced splicing to background splicing of 37R3-2 observed in yeast cells. The inteins evolved at 30° C. also exhibit similarly improved (~2- to 6-fold) splicing kinetics and splicing efficiencies at 12 and 24 hours relative to that of inteins 2-4 and 3-2 (FIG. 3C). The best 30° C. library clone (30R3-1) generated 72% spliced GFP after 24 hours, compared with 33% and 19% spliced GFP for the 3-2 and 2-4 inteins, respectively, while splicing with ≤3% efficiency in the absence of 4-HT (FIG. 3C).

Interestingly, the fraction of protein splicing that was completed by 12 hours relative to an endpoint of 24 hours was also greater for the newly evolved inteins compared with the 2-4 and 3-2 inteins. For example, an average of 59% of the total amount of spliced GFP in mammalian cells after 24 hours was present after 12 hours among the three 37° C. library clones, and an average of 57% of the total amount of spliced GFP after 24 hours was present after 12 hours among the three 30° C. library clones. For comparison, 45% and 31% of the total spliced GFP after 24 hours was present at 12 hours for the 3-2 and 2-4 inteins, respectively. These results collectively indicate that in live mammalian cells at 37° C. the newly evolved inteins exhibit increased splicing rate and higher extent of splicing compared with the original evolved inteins, while maintaining low background splicing in the absence of 4-HT.

Evolved Intein Properties in Different Proteins in Mammalian Cells

Figure 8:
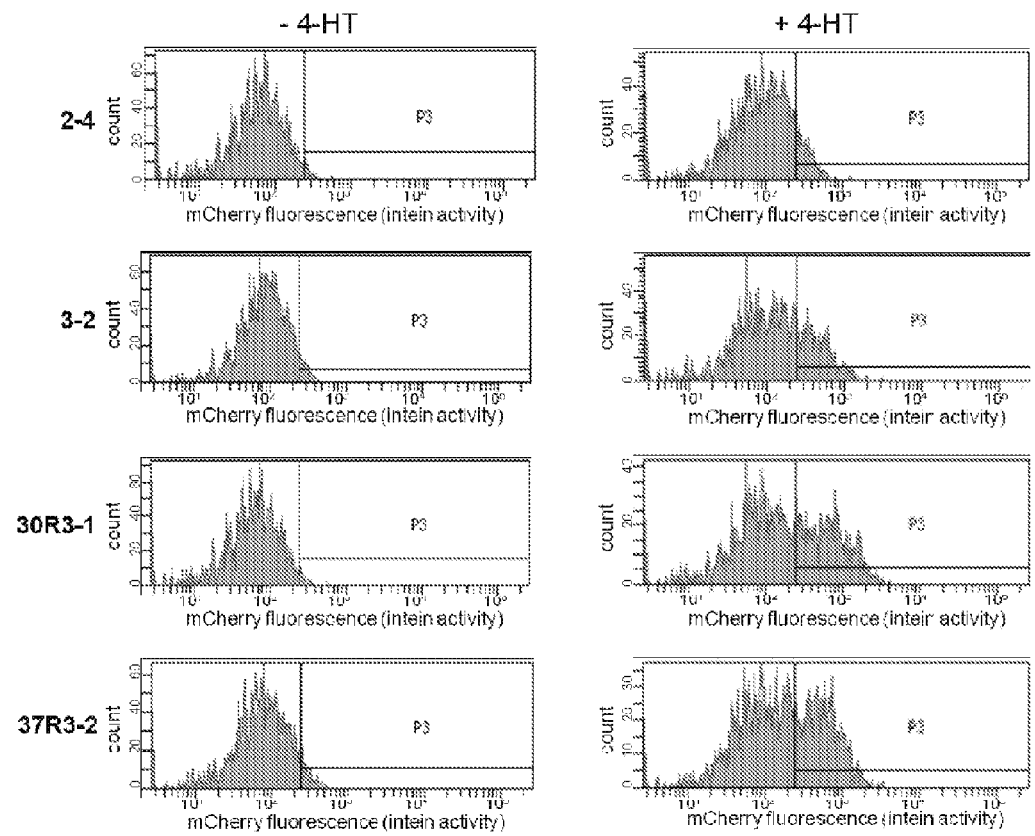
FIG. 8. Characterization of the 30R3-1 (SEQ ID NO: 3) and 37R3-2 (SEQ ID NO: 7) evolved inteins in the mCherry context in mammalian cells by flow cytometry. Representative FACS plots of HEK293 cells transfected with DNA expressing the 2-4 (SEQ ID NO: 1), 3-2 (SEQ ID NO: 2), 30R3-1 (SEQ ID NO: 3), or 37R3-2 (SEQ ID NO: 7) inteins in the context of mCherry, without 4-HT or treated with 1 μM 4-HT for 24 h at 37° C. are shown. The P3 analysis gate indicates the cell population that is positive for mCherry fluorescence.

The generality of 4-HT-dependent splicing of the two best evolved inteins (30R3-1 and 37R3-2) was investigated by inserting these inteins into three other protein contexts in addition to GFP in mammalian cells. The inteins were inserted into mCherry, a red fluorescent protein, in place of Thr 113, the residue in mCherry that corresponds to the Cys residue used for intein insertion in GFP. As in the case of GFP, this placement positions the intein near the mid-point of a β-strand and abolishes mCherry fluorescence until splicing takes place (vide infra). The corresponding genes were introduced into HEK293 cells as described above for the GFP-intein genes, then treated with media containing 1 µM 4-HT or with media lacking 4-HT. These cells were incubated at 37° C. for an additional 12 to 24 hours, then harvested for FACS (FIG. 8) and Western blot analysis.

Figure 4:
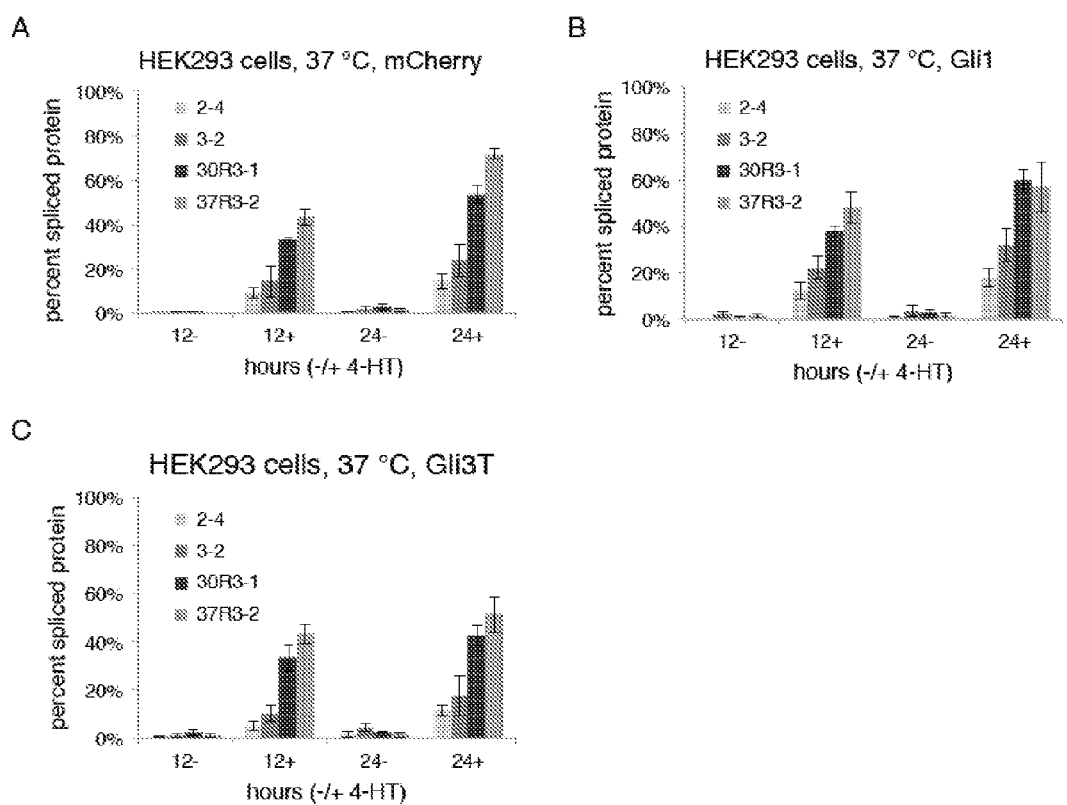
FIG. 4. Splicing characteristics of the 30R3-1 and 37R3-2 evolved inteins in mammalian cells in three different protein contexts. HEK293 cells expressing the inteins shown in the context of mCherry (A), Gli1 (B), or Gli3T (C) were incubated for 12 h or 24 h in the presence or absence of 1 μM 4-HT. Unspliced and spliced protein was quantitated as described in FIG. 3. Error bars represent the standard deviation of at least three independent experiments.

Both of the 37R3-2 and the 30R3-1 evolved inteins continued to exhibit significant improvement in splicing performance over the 2-4 and 3-2 inteins in the context of mCherry (FIG. 4A). The 37R3-2 intein resulted in 72% spliced mCherry protein after 24 hours and 43% spliced protein after 12 hours. The 30R3-1 intein resulted in 54% and 33% spliced mCherry after 24 and 12 hours, respectively. Thus the percentage of spliced mCherry generated by the 37R3-2 intein at 24 hours or 12 hours was ~3-fold higher than that of 3-2 intein, and ~5-fold higher than that of the 2-4 intein. Background splicing in the absence of 4-HT was ≤3% for all inteins assayed in this context.

The splicing characteristics of the newly evolved inteins was investigated in the contexts of two additional mammalian proteins, Gli1 and Gli3T. Gli1 and Gli3 are transcription factors that mediate Hedgehog signaling (Koebernick and Pieler, 2002) and are important in many key developmental processes such as spinal cord patterning (Bai et al., 2004) and limb development (Barna et al., 2005). Gli3T is a C-terminally truncated form of the transcription factor Gli3 that is used as a transcriptional repressor (Wang et al., 2000). Gli1 and Gli3T are large proteins, 122 kDa and 85 kDa respectively, and are both structurally unrelated to GFP, mCherry, and structurally distinct from each other. The 37R3-2 and 30R3-1 inteins were inserted genetically in place of Cys 273 of the Gli1 protein and in place of Cys 515 of the Gli3T protein as described previously (Yuen et al., 2006). The insertion of inteins into these proteins at these positions abolishes their activities until splicing takes place (Yuen et al., 2006). The resulting constructs were introduced into HEK293 cells and splicing was evaluated by Western blot as described above.

Consistent with their enhanced performance characteristics in the GFP and mCherry contexts, the newly evolved inteins in Gli1 and in Gli3T resulted in significantly higher (~2- to 4-fold in Gli1, and ~3- to 8-fold in Gli3T) percentages of spliced protein compared with the 3-2 or 2-4 inteins (FIGS. 4B and 4C). Up to 48% and 60% of Gli1 protein was spliced by the newly evolved inteins after 12 and 24 hours, respectively, while the previously evolved 3-2 intein resulted in 22% and 32% splicing under the same conditions. Likewise, the newly evolved inteins generated up to 43% and 51% spliced Gli3T protein after 12 and 24 hours, compared with 10% and 18% for the 3-2 intein.

It was previously noted (Yuen et al., 2006; unpublished data) that the 3-2 intein undergoes background splicing in the absence of 4-HT to a greater extent than the 2-4 intein, and the Gli1 and Gli3T data in FIGS. 4B and 4C replicated these observations. The background splicing of newly evolved clone 37R3-2 across all four proteins tested (GFP, mCherry, Gli1, and Gli3T) is very low and often was not detectable. Clone 30R3-1 in general resulted in a slightly higher degree of background splicing, but this level of splicing in the absence of 4-HT remained ≤3% in all four proteins tested in this work, and generally was similar to or slightly lower than the background splicing of the 3-2 intein. Taken together, these results establish the overall superior splicing kinetics and splicing efficiency without significant background splicing for both newly evolved inteins 37R3-2 and 30R3-1 in a variety of protein contexts in mammalian cells.

Mutational Analysis of Evolved Inteins 30R3-1 and 37R3-2

To probe which mutations were responsible for the improved properties of evolved inteins 30R3-1 and 37R3-2, each of the mutations (five in 30R3-1 and four in 37R3-2) was systematically reverted to the corresponding amino acid present in the original 3-2 intein. Each of these reversion mutants was inserted genetically into GFP and transformed into RDY98 yeast cells. Protein expression was induced for 24 hours at 30° C. and the resulting cells were incubated for six hours in the presence or absence of 4-HT at 30° C. and 37° C. Protein splicing was assessed by FACS and Western blot analysis as described above.

Compared with the 3-2 intein, both newly evolved intein variants contain Val34Ala and Thr328Lys mutations. These two changes also correspond to the two differences between the 2-4 intein and the 3-2 intein, which evolved from the 2-4 intein. In both newly evolved inteins the amino acids at these two positions were the residues present in the 2-4 intein. Consistent with the lower splicing activity in the absence or presence of 4-HT of the 2-4 intein relatively to the 3-2 intein, the reversion of Ala34 back to Val and Lys328 back to Thr resulted in significantly higher background splicing, especially in the 37R3-2 intein, together with slightly higher splicing efficiency in the presence of 4-HT (FIGS. 5A-5D). These results suggest that residues 34 and 328 in the newly evolved inteins modestly modulate splicing activity in a ligand-independent manner, and that the presence of Ala34 and Lys328 serves to decrease background splicing by a significant fraction (~2- to 4-fold), while lowering splicing efficiency in the presence of 4-HT by a much smaller relative fraction (~10% lower).

The Glu375Gly mutation was also present in both the 30R3-1 and the 37R3-2 inteins. Reversion of this mutation resulted in substantially increased (2- to 10-fold) background splicing in the absence of 4-HT without any significant change in splicing efficiency in the presence of 4-HT (FIGS. 5A-5D). This mutation therefore likely serves to suppress splicing activity in a manner that is selective for the conformation of the ligand-free intein.

Figure 5:
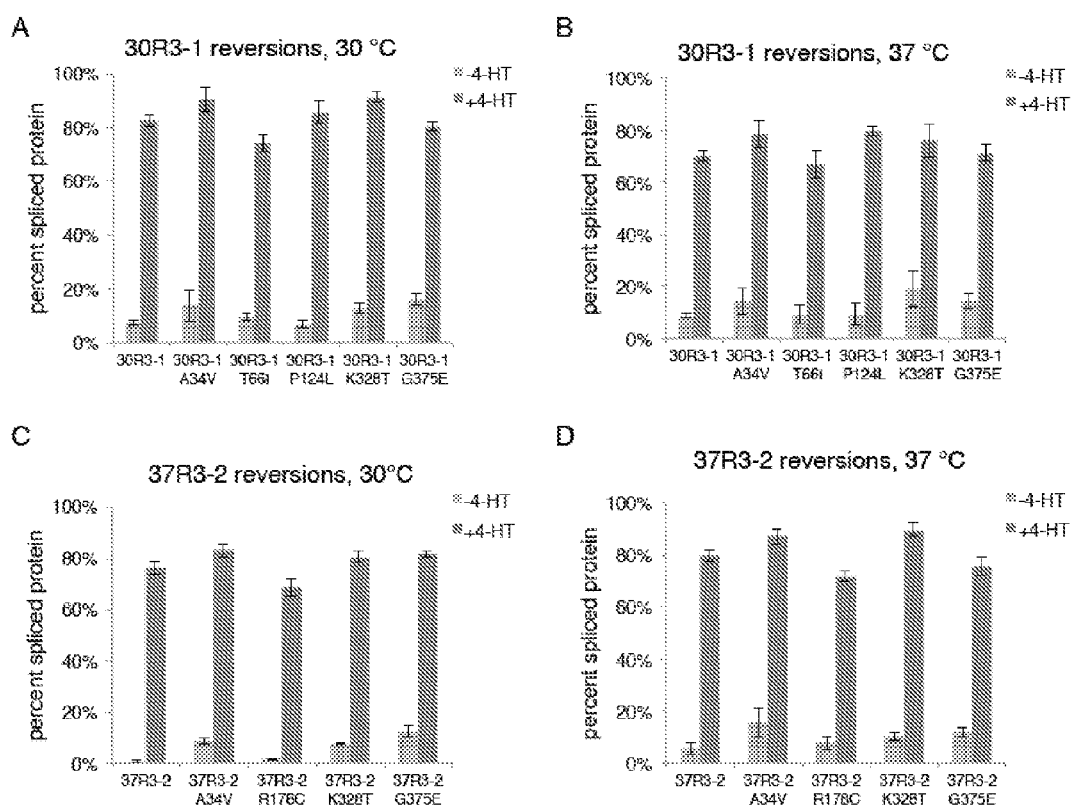
FIG. 5. Reversion mutant analysis of evolved inteins 30R3-1 (SEQ ID NO: 3) and 37R3-2 (SEQ ID NO: 7). Each mutation in 30R3-1 (SEQ ID NO: 3) ((A) and (B)) and 37R3-2 (SEQ ID NO: 7) ((C) and (D)) relative to the original 3-2 intein (SEQ ID NO: 2) was reverted separately and the resulting intein variants in the context of GFP were characterized in yeast cells at 30° C. ((A) and (C)) and at 37° C. ((B) and (D)). Yeast cell lysates were prepared and analyzed by Western blot and densitometry after 6 hours as described in FIG. 2. Error bars represent the standard deviation of at least three independent experiments.

Among the other two mutations in 30R3-1, neither was present in 37R3-2. Reverting the Thr at residue 66 to Ile in 30R3-1 resulted in no significant change in intein activity other than a slight decrease in 4-HT-triggered splicing at 30° C. (FIG. 5A). Likewise, reversion of Pro124 to Leu also resulted in similar splicing activities in the presence or absence of 4-HT as the 30R3-1 intein (FIGS. 5A and 5B). These results suggest that Thr66 and Pro124 may not contribute to the observed changes in splicing activity, or may only contribute to improved splicing in combination with one or more additional mutations.

The Cys178Arg mutation is the sole change in 37R3-2 that is not present in 30R3-1. Reversion of this mutation modestly decreases splicing efficiency in the presence of 4-HT and may also slightly increase background splicing (FIGS. 5C and 5D). Interestingly, these results suggest that no single mutation in the 30R3-1 or 37R3-2 inteins is responsible for the substantial majority of the observed ~2- to 5-fold improved splicing of GFP in yeast at 30° C. or 37° C. compared with the parental 2-4 or 3-2 inteins. Instead, the observations described herein suggest that the combination of four or five mutations, each of which contribute modest improvements, cumulatively result in the substantially faster and more efficient splicing in the presence of 4-HT while preserving or decreasing the extent of background splicing relative to the 3-2 intein.

Discussion

The intein evolution efforts described here were performed under the hypothesis that inteins evolved under more stringent selection conditions and at 37° C. may yield ligand-dependent inteins with superior splicing yields, faster splicing kinetics, and/or lower background-splicing than those previously reported. Parallel 37° C. and 30° C. screening conditions were used to explore a wider range of possible advantageous mutations than might have been surveyed through 37° C. screens alone. Indeed, mutations in the two evolved inteins with the best overall properties, clones 30R3-1 and 37R3-2, arose from both the 30° C. and 37° C. libraries. These two inteins in the presence of 4-HT exhibited substantially higher yields of spliced protein and faster splicing, while maintaining comparable or slightly improved (decreased) amounts of background splicing in the absence of 4-HT.

It is interesting that the newly evolved inteins exhibited faster splicing kinetics (i.e., reached a higher percentage of final spliced protein levels at early time points) compared with the parental inteins even though the methods used in this work did not explicitly screen for improved splicing kinetics. It is possible that some of the mutations discovered in this work improve the kinetics of the splicing reaction itself, but it is equally likely that these mutations increased the rate of other steps in the ligand-induced splicing process such as protein folding, binding or dissociation from Hsp90 or other proteins (Feil et al., 1996; Kellendonk et al., 1996; Zhang et al., 1996; Danielian et al., 1998; Picard et al., 2000; Buskirk et al., 2004; Yuen et al., 2006), or conformational changes that influence the ability of the intein to undergo splicing.

The FACS-based screening method used here, in which intein activity is coupled to an increase in GFP fluorescence, is ideally suited for this type of laboratory evolution in which starting proteins possessing detectable activities are evolved to higher levels of activity under specific sets of conditions. FACS offers a large dynamic range that is crucial for distinguishing active and highly active library members, allows analysis of individual library members at the single-cell level, and supports very high-throughput screens; in this work, ~$10^7$ cells were screened in a few hours. FACS is also a nondestructive method, and yeast cells collected in this manner are robust enough to be cultured in liquid or on solid media immediately following the screening process. The ability to culture and thus amplify the cells resulting from each screen simplifies the process of enriching desired library members. These features together enabled improved variants to emerge by tuning the screen to capture progressively more fluorescent cells with progressively higher intein activity levels.

The use of small molecules to modulate protein structure post-translationally in living cells remains an attractive approach to studying protein function. The ligand-dependent intein, like other post-translationally triggered protein manipulation methods (Stankunas et al., 2003; Wang et al., 2003; Bayle et al., 2006), facilitates temporal control of protein structure as well as dose-dependent titration of spliced protein levels (Buskirk et al., 2004; Yuen et al., 2006). Inteins offer some features that may make them particularly well suited for certain applications, especially given the improvements in splicing characteristics described herein. While traditional chemical genetic approaches require the discovery of small molecules that perturb the activity of each protein of interest, ligand-dependent inteins confer dependence on a single small molecule (e.g., 4-HT) on a variety of proteins of interest with single-target specificity. The protein splicing process leaves behind only a single Cys residue, or no scar in cases in which the target protein naturally contains a Cys residue in a location that results in loss of protein function upon intein insertion. Moreover, small-molecule-triggered protein splicing is pseudo-autocatalytic and does not require additional cellular components or specific conditions that may not be easy to establish for some intracellular proteins.

The small-molecule-dependent inteins developed here may be particularly suited for studying signaling pathways because of the minimal cellular perturbations required to achieve control over protein function. The use of the evolved inteins does not require changes to regulatory regions of genes and does not require the expression of any other proteins or nucleic acids. Since cell disruption is minimized, proteins that are a part of complex mammalian signaling pathways—for example those in which feedback regulation plays a significant role—have a greater chance of maintaining their native regulatory networks. Further, the dose-dependent nature of ligand-dependent intein-splicing allows for the fine control of functional protein levels.

REFERENCES

Acar, M., Pando, B. F., Arnold, F. H., Elowitz, M. B., and van Oudenaarden, A. (2010). A general mechanism for network-dosage compensation in gene circuits. Science 329, 1656-1660.

Bai, C. B., Stephen, D., and Joyner, A. L. (2004). All mouse ventral spinal cord patterning by hedgehog is Gli dependent and involves an activator function of Gli3. Dev Cell 6, 103-115.

Banaszynski, L. A., Chen, L. C., Maynard-Smith, L. A., Ooi, A. G., and Wandless, T. J. (2006). A rapid, reversible, and tunable method to regulate protein function in living cells using synthetic small molecules. Cell 126, 995-1004.

Banaszynski, L. A., and Wandless, T. J. (2006). Conditional control of protein function. Chem Biol 13, 11-21.

Barna, M., Pandolfi, P. P., and Niswander, L. (2005). Gli3 and Plzf cooperate in proximal limb patterning at early stages of limb development. Nature 436, 277-281.

Bayle, J. H., Grimley, J. S., Stankunas, K., Gestwicki, J. E., Wandless, T. J., and Crabtree, G. R. (2006). Rapamycin analogs with differential binding specificity permit orthogonal control of protein activity. Chem Biol 13, 99-107.

Buskirk, A. R., and Liu, D. R. (2005). Creating small-molecule-dependent switches to modulate biological functions. Chem Biol 12, 151-161.

Buskirk, A. R., Ong, Y. C., Gartner, Z. J., and Liu, D. R. (2004). Directed evolution of ligand dependence: small-molecule-activated protein splicing. Proc Natl Acad Sci USA 101, 10505-10510.

Danielian, P. S., Muccino, D., Rowitch, D. H., Michael, S. K., and McMahon, A. P. (1998). Modification of gene activity in mouse embryos in utero by a tamoxifen-inducible form of Cre recombinase. Curr Biol 8, 1323-1326.

Feil, R., Brocard, J., Mascrez, B., LeMeur, M., Metzger, D., and Chambon, P. (1996). Ligand-activated site-specific recombination in mice. Proc Natl Acad Sci USA 93, 10887-10890.

Fire, A., Xu, S., Montgomery, M. K., Kostas, S. A., Driver, S. E., and Mello, C. C. (1998). Potent and specific genetic interference by double-stranded RNA in *Caenorhabditis elegans*. Nature 391, 806-811.

Gibson, D. G., Young, L., Chuang, R. Y., Venter, J. C., Hutchison, C. A., 3rd, and Smith, H. O. (2009). Enzymatic assembly of DNA molecules up to several hundred kilobases. Nat Methods 6, 343-345.

Gossen, M., and Bujard, H. (1992). Tight control of gene expression in mammalian cells by tetracycline-responsive promoters. Proc Natl Acad Sci USA 89, 5547-5551. Hartley, P. D., and Madhani, H. D. (2009). Mechanisms that specify promoter nucleosome location and identity. Cell 137, 445-458.

Kellendonk, C., Tronche, F., Monaghan, A. P., Angrand, P. O., Stewart, F., and Schutz, G. (1996). Regulation of Cre recombinase activity by the synthetic steroid RU 486. Nucleic Acids Res 24, 1404-1411.

Kino, T., Hatanaka, H., Miyata, S., Inamura, N., Nishiyama, M., Yajima, T., Goto, T., Okuhara, M., Kohsaka, M., Aoki, H., et al. (1987). FK-506, a novel immunosuppressant isolated from a Streptomyces. II. Immunosuppressive effect of FK-506 in vitro. J Antibiot (Tokyo) 40, 1256-1265.

Koebernick, K., and Pieler, T. (2002). Gli-type zinc finger proteins as bipotential transducers of Hedgehog signaling. Differentiation 70, 69-76.

Lew, B. M., and Paulus, H. (2002). An in vivo screening system against protein splicing useful for the isolation of non-splicing mutants or inhibitors of the RecA intein of *Mycobacterium tuberculosis*. Gene 282, 169-177.

Marschang, P., Brich, J., Weeber, E. J., Sweatt, J. D., Shelton, J. M., Richardson, J. A., Hammer, R. E., and Herz, J. (2004). Normal development and fertility of knockout mice lacking the tumor suppressor gene LRP1b suggest functional compensation by LRP1. Mol Cell Biol 24, 3782-3793.

Mootz, H. D., Blum, E. S., and Muir, T. W. (2004). Activation of an autoregulated protein kinase by conditional protein splicing. Angew Chem Int Ed Engl 43, 5189-5192.

Mootz, H. D., Blum, E. S., Tyszkiewicz, A. B., and Muir, T. W. (2003). Conditional protein splicing: a new tool to control protein structure and function in vitro and in vivo. J Am Chem Soc 125, 10561-10569.

Mootz, H. D., and Muir, T. W. (2002). Protein splicing triggered by a small molecule. J Am Chem Soc 124, 9044-9045.

Ormo, M., Cubitt, A. B., Kallio, K., Gross, L. A., Tsien, R. Y., and Remington, S. J. (1996). Crystal structure of the *Aequorea victoria* green fluorescent protein. Science 273, 1392-1395.

Paulus, H. (2000). Protein splicing and related forms of protein autoprocessing. Annu Rev Biochem 69, 447-496.

Picard, D. (2000). Posttranslational regulation of proteins by fusions to steroid-binding domains. Methods Enzymol 327, 385-401.

Pratt, M. R., Schwartz, E. C., and Muir, T. W. (2007). Small-molecule-mediated rescue of protein function by an inducible proteolytic shunt. Proc Natl Acad Sci USA 104, 11209-11214. Raymond, C. K., Pownder, T. A., and Sexson, S. L. (1999). General method for plasmid construction using homologous recombination. Biotechniques 26, 134-138, 140-131.

Sauer, B., and Henderson, N. (1988). Site-specific DNA recombination in mammalian cells by the Cre recombinase of bacteriophage P1. Proc Natl Acad Sci USA 85, 5166-5170.

Schneekloth, J. S., Jr., Fonseca, F. N., Koldobskiy, M., Mandal, A., Deshaies, R., Sakamoto, K., and Crews, C. M. (2004). Chemical genetic control of protein levels: selective in vivo targeted degradation. J Am Chem Soc 126, 3748-3754.

Schreiber, S. L. (2003). The small-molecule approach to biology: Chemical genetics and diversityoriented organic synthesis make possible the systematic exploration of biology. In Chem Eng News, pp. 51-61.

Schwartz, E. C., Saez, L., Young, M. W., and Muir, T. W. (2007). Post-translational enzyme activation in an animal via optimized conditional protein splicing. Nat Chem Biol 3, 50-54.

Shi, J., and Muir, T. W. (2005). Development of a tandem protein trans-splicing system based on native and engineered split inteins. J Am Chem Soc 127, 6198-6206.

Shogren-Knaak, M. A., Alaimo, P. J., and Shokat, K. M. (2001). Recent advances in chemical approaches to the study of biological systems. Annu Rev Cell Dev Biol 17, 405-433.

Stankunas, K., Bayle, J. H., Gestwicki, J. E., Lin, Y. M., Wandless, T. J., and Crabtree, G. R. (2003). Conditional protein alleles using knockin mice and a chemical inducer of dimerization. Mol Cell 12, 1615-1624.

Wang, B., Fallon, J. F., and Beachy, P. A. (2000). Hedgehog-regulated processing of Gli3 produces an anterior/posterior repressor gradient in the developing vertebrate limb. Cell 100, 423-434.

Wang, H., Shimizu, E., Tang, Y. P., Cho, M., Kyin, M., Zuo, W., Robinson, D. A., Alaimo, P. J., Zhang, C., Morimoto, H., et al. (2003). Inducible protein knockout reveals temporal requirement of CaMKII reactivation for memory consolidation in the brain. Proc Natl Acad Sci USA 100, 4287-4292.

Wong, S. L., and Roth, F. P. (2005). Transcriptional compensation for gene loss plays a minor role in maintaining genetic robustness in *Saccharomyces cerevisiae*. Genetics 171, 829-833.

Xu, M. Q., Southworth, M. W., Mersha, F. B., Hornstra, L. J., and Perler, F. B. (1993). In vitro protein splicing of purified precursor and the identification of a branched intermediate. Cell 75, 1371-1377.

Yuen, C. M., Rodda, S. J., Vokes, S. A., McMahon, A. P., and Liu, D. R. (2006). Control of transcription factor activity and osteoblast differentiation in mammalian cells using an evolved small-molecule dependent intein. J Am Chem Soc 128, 8939-8946.

Zaccolo, M., Williams, D. M., Brown, D. M., and Gherardi, E. (1996). An approach to random mutagenesis of DNA using mixtures of triphosphate derivatives of nucleoside analogues. J Mol Biol 255, 589-603.

Zhang, Y., Riesterer, C., Ayrall, A. M., Sablitzky, F., Littlewood, T. D., and Reth, M. (1996). Inducible site-directed recombination in mouse embryonic stem cells. Nucleic Acids Res 24, 543-548.

Zhao, H., and Zha, W. (2006). In vitro 'sexual' evolution through the PCR-based staggered extension process (StEP). Nat Protoc 1, 1865-1871.

All publications, patents and sequence database entries mentioned herein, including those listed in the Summary, Detailed Description, Examples, and References sections above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

It is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim.

Where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where ranges are given, endpoints are included, and, if not otherwise indicated or inconsistent, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

SEQUENCE LISTING

```
<160> NUMBER OF SEQ ID NOS: 39

<210> SEQ ID NO 1
<211> LENGTH: 413
<212> TYPE: PRT
<213> ORGANISM: Artificial Sequence
<220> FEATURE:
```

<223> OTHER INFORMATION: artificial polypeptide

<400> SEQUENCE: 1

```
Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400
```

His Thr Leu Val Ala Glu Gly Val Val His Asn Cys
            405                 410

<210> SEQ ID NO 2
<211> LENGTH: 413
<212> TYPE: PRT
<213> ORGANISM: Artificial Sequence
<220> FEATURE:
<223> OTHER INFORMATION: artificial polypeptide

<400> SEQUENCE: 2

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Val Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln His Gln Arg Leu Ala Gln Leu
    290                 295                 300

Leu Leu Ile Leu Ser His Ile Arg His Met Ser Asn Lys Gly Met Glu
305                 310                 315                 320

His Leu Tyr Ser Met Lys Tyr Thr Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Lys Phe Leu
        355                 360                 365

His Asp Met Leu Ala Glu Glu Leu Arg Tyr Ser Val Ile Arg Glu Val
370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410

<210> SEQ ID NO 3
<211> LENGTH: 413
<212> TYPE: PRT
<213> ORGANISM: Artificial Sequence
<220> FEATURE:
<223> OTHER INFORMATION: artificial polypeptide

<400> SEQUENCE: 3

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Pro Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
    290                 295                 300

```
Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Gly Leu Arg Tyr Ser Val Ile Arg Glu Val
    370                 375                 380

Leu Pro Thr Arg Arg Ala Arg Thr Phe Asp Leu Glu Val Glu Leu
385                 390                 395                 400

His Thr Leu Val Ala Glu Gly Val Val Val His Asn Cys
                405                 410

<210> SEQ ID NO 4
<211> LENGTH: 413
<212> TYPE: PRT
<213> ORGANISM: Artificial Sequence
<220> FEATURE:
<223> OTHER INFORMATION: artificial polypeptide

<400> SEQUENCE: 4

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255
```

```
Thr Phe Leu Ser Ser Thr Leu Lys Ser Leu Glu Glu Lys Asp His Ile
                260                 265                 270

His Arg Ala Leu Asp Lys Ile Thr Asp Thr Leu Ile His Leu Met Ala
            275                 280                 285

Lys Ala Gly Leu Thr Leu Gln Gln Gln His Gln Arg Leu Ala Gln Leu
        290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
    370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410

<210> SEQ ID NO 5
<211> LENGTH: 413
<212> TYPE: PRT
<213> ORGANISM: Artificial Sequence
<220> FEATURE:
<223> OTHER INFORMATION: artificial polypeptide

<400> SEQUENCE: 5

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
                20                  25                  30

Ala Ala Ala Lys Asp Gly Thr Leu Leu Ala Arg Pro Val Val Ser Trp
            35                  40                  45

Phe Asp Gln Gly Thr Arg Asp Val Ile Gly Leu Arg Ile Ala Gly Gly
        50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Pro Tyr Ser Glu Tyr
        115                 120                 125

Asp Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Cys Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205
```

```
Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Gly Leu Arg Tyr Ser Val Ile Arg Glu Val
370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410

<210> SEQ ID NO 6
<211> LENGTH: 413
<212> TYPE: PRT
<213> ORGANISM: Artificial Sequence
<220> FEATURE:
<223> OTHER INFORMATION: artificial polypeptide

<400> SEQUENCE: 6

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asn Pro Thr Ser Pro Phe Ser Glu Ala Ser Met Met Gly Leu Leu Thr
    130                 135                 140

Asn Leu Ala Asp Arg Glu Leu Val His Met Ile Asn Trp Ala Lys Arg
145                 150                 155                 160
```

Val Pro Gly Phe Val Asp Leu Thr Leu His Asp Gln Ala His Leu Leu
            165                 170                 175

Glu Arg Ala Trp Leu Glu Ile Leu Met Ile Gly Leu Val Trp Arg Ser
        180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
    210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
        290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Gly Leu Arg Tyr Ser Val Ile Arg Glu Val
        370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410

<210> SEQ ID NO 7
<211> LENGTH: 413
<212> TYPE: PRT
<213> ORGANISM: Artificial Sequence
<220> FEATURE:
<223> OTHER INFORMATION: artificial polypeptide

<400> SEQUENCE: 7

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Thr Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gly Pro
                85                  90                  95

Gly Gly Ser Gly Asn Ser Leu Ala Leu Ser Leu Thr Ala Asp Gln Met
            100                 105                 110

```
Val Ser Ala Leu Leu Asp Ala Glu Pro Pro Ile Leu Tyr Ser Glu Tyr
            115                 120                 125

Asp Pro Thr Ser Pro Phe Ser Glu Ala Ser Met Met Gly Leu Leu Thr
130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Arg Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln His Gln Arg Leu Ala Gln Leu
290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Asp Lys Phe Leu
        355                 360                 365

His Asp Met Leu Ala Glu Glu Leu Arg Tyr Ser Val Ile Arg Glu Val
370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410

<210> SEQ ID NO 8
<211> LENGTH: 413
<212> TYPE: PRT
<213> ORGANISM: Artificial Sequence
<220> FEATURE:
<223> OTHER INFORMATION: artificial polypeptide

<400> SEQUENCE: 8

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Val Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60
```

```
Ala Thr Val Trp Ala Thr Pro Asp His Lys Val Leu Thr Glu Tyr Gly
 65                  70                  75                  80

Trp Arg Ala Ala Gly Glu Leu Arg Lys Gly Asp Arg Val Ala Gly Pro
                 85                  90                  95

Gly Gly Ser Gly Asn Ser Leu Ala Leu Ser Leu Thr Ala Asp Gln Met
            100                 105                 110

Val Ser Ala Leu Leu Asp Ala Glu Pro Pro Ile Leu Tyr Ser Glu Tyr
        115                 120                 125

Asp Pro Thr Ser Pro Phe Ser Glu Ala Ser Met Met Gly Leu Leu Thr
130                 135                 140

Asn Leu Ala Asp Arg Glu Leu Val His Met Ile Asn Trp Ala Lys Arg
145                 150                 155                 160

Val Pro Gly Phe Val Asp Leu Thr Leu His Asp Gln Ala His Leu Leu
                165                 170                 175

Glu Arg Ala Trp Leu Glu Ile Leu Met Ile Gly Leu Val Trp Arg Ser
            180                 185                 190

Met Glu His Pro Gly Lys Leu Leu Phe Ala Pro Asn Leu Leu Leu Asp
        195                 200                 205

Arg Asn Gln Gly Lys Cys Val Glu Gly Met Val Glu Ile Phe Asp Met
210                 215                 220

Leu Leu Ala Thr Ser Ser Arg Phe Arg Met Met Asn Leu Gln Gly Glu
225                 230                 235                 240

Glu Phe Val Cys Leu Lys Ser Ile Ile Leu Leu Asn Ser Gly Val Tyr
                245                 250                 255

Thr Phe Leu Ser Ser Thr Leu Lys Ser Leu Glu Glu Lys Asp His Ile
            260                 265                 270

His Arg Ala Leu Asp Lys Ile Thr Asp Thr Leu Ile His Leu Met Ala
        275                 280                 285

Lys Ala Gly Leu Thr Leu Gln Gln Gln His Gln Arg Leu Ala Gln Leu
290                 295                 300

Leu Leu Ile Leu Ser His Ile Arg His Met Ser Asn Lys Gly Met Glu
305                 310                 315                 320

His Leu Tyr Ser Met Lys Tyr Lys Asn Val Val Pro Leu Tyr Asp Leu
                325                 330                 335

Leu Leu Glu Met Leu Asp Ala His Arg Leu His Ala Gly Gly Ser Gly
            340                 345                 350

Ala Ser Arg Val Gln Ala Phe Ala Asp Ala Leu Asp Lys Phe Leu
        355                 360                 365

His Asp Met Leu Ala Glu Glu Leu Arg Tyr Ser Val Ile Arg Glu Val
370                 375                 380

Leu Pro Thr Arg Arg Ala Arg Thr Phe Asp Leu Glu Val Glu Glu Leu
385                 390                 395                 400

His Thr Leu Val Ala Glu Gly Val Val Val His Asn Cys
                405                 410

<210> SEQ ID NO 9
<211> LENGTH: 152
<212> TYPE: PRT
<213> ORGANISM: Artificial Sequence
<220> FEATURE:
<223> OTHER INFORMATION: artificial polypeptide

<400> SEQUENCE: 9

Cys Leu Ala Glu Gly Thr Arg Ile Phe Asp Pro Val Thr Gly Thr Thr
 1               5                  10                  15
```

```
His Arg Ile Glu Asp Val Val Asp Gly Arg Lys Pro Ile His Val Val
            20                  25                  30

Ala Val Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
 65                  70                  75                  80

Trp Arg Ala Ala Gly Glu Leu Arg Lys Gly Asp Arg Val Ala Arg Val
                85                  90                  95

Gln Ala Phe Ala Asp Ala Leu Asp Lys Phe Leu His Asp Met Leu
            100                 105                 110

Ala Glu Glu Leu Arg Tyr Ser Val Ile Arg Glu Val Leu Pro Thr Arg
            115                 120                 125

Arg Ala Arg Thr Phe Asp Leu Glu Val Glu Leu His Thr Leu Val
        130                 135                 140

Ala Glu Gly Val Val Val His Asn
145                 150

<210> SEQ ID NO 10
<211> LENGTH: 94
<212> TYPE: PRT
<213> ORGANISM: Artificial Sequence
<220> FEATURE:
<223> OTHER INFORMATION: artificial polypeptide

<400> SEQUENCE: 10

Cys Leu Ala Glu Gly Thr Arg Ile Phe Asp Pro Val Thr Gly Thr Thr
  1               5                  10                  15

His Arg Ile Glu Asp Val Val Asp Gly Arg Lys Pro Ile His Val Val
            20                  25                  30

Ala Val Ala Lys Asp Gly Thr Leu Leu Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
 65                  70                  75                  80

Trp Arg Ala Ala Gly Glu Leu Arg Lys Gly Asp Arg Val Ala
                85                  90

<210> SEQ ID NO 11
<211> LENGTH: 58
<212> TYPE: PRT
<213> ORGANISM: Artificial Sequence
<220> FEATURE:
<223> OTHER INFORMATION: artificial polypeptide

<400> SEQUENCE: 11

Arg Val Gln Ala Phe Ala Asp Ala Leu Asp Asp Lys Phe Leu His Asp
  1               5                  10                  15

Met Leu Ala Glu Glu Leu Arg Tyr Ser Val Ile Arg Glu Val Leu Pro
            20                  25                  30

Thr Arg Arg Ala Arg Thr Phe Asp Leu Glu Val Glu Glu Leu His Thr
        35                  40                  45

Leu Val Ala Glu Gly Val Val Val His Asn
    50                  55

<210> SEQ ID NO 12
```

```
<211> LENGTH: 248
<212> TYPE: PRT
<213> ORGANISM: Artificial Sequence
<220> FEATURE:
<223> OTHER INFORMATION: artificial polypeptide

<400> SEQUENCE: 12

Asn Ser Leu Ala Leu Ser Leu Thr Ala Asp Gln Met Val Ser Ala Leu
1               5                   10                  15

Leu Asp Ala Glu Pro Pro Ile Leu Tyr Ser Glu Tyr Asp Pro Thr Ser
            20                  25                  30

Pro Phe Ser Glu Ala Ser Met Met Gly Leu Leu Thr Asn Leu Ala Asp
        35                  40                  45

Arg Glu Leu Val His Met Ile Asn Trp Ala Lys Arg Val Pro Gly Phe
    50                  55                  60

Val Asp Leu Thr Leu His Asp Gln Ala His Leu Leu Glu Cys Ala Trp
65                  70                  75                  80

Leu Glu Ile Leu Met Ile Gly Leu Val Trp Arg Ser Met Glu His Pro
                85                  90                  95

Gly Lys Leu Leu Phe Ala Pro Asn Leu Leu Leu Asp Arg Asn Gln Gly
            100                 105                 110

Lys Cys Val Glu Gly Met Val Glu Ile Phe Asp Met Leu Leu Ala Thr
        115                 120                 125

Ser Ser Arg Phe Arg Met Met Asn Leu Gln Gly Glu Glu Phe Val Cys
    130                 135                 140

Leu Lys Ser Ile Ile Leu Leu Asn Ser Gly Val Tyr Thr Phe Leu Ser
145                 150                 155                 160

Ser Thr Leu Lys Ser Leu Glu Glu Lys Asp His Ile His Arg Ala Leu
                165                 170                 175

Asp Lys Ile Thr Asp Thr Leu Ile His Leu Met Ala Lys Ala Gly Leu
            180                 185                 190

Thr Leu Gln Gln Gln His Gln Arg Leu Ala Gln Leu Leu Leu Ile Leu
        195                 200                 205

Ser His Ile Arg His Met Ser Asn Lys Gly Met Glu His Leu Tyr Ser
    210                 215                 220

Met Lys Tyr Thr Asn Val Val Pro Leu Tyr Asp Leu Leu Leu Glu Met
225                 230                 235                 240

Leu Asp Ala His Arg Leu His Ala
                245

<210> SEQ ID NO 13
<211> LENGTH: 248
<212> TYPE: PRT
<213> ORGANISM: Artificial Sequence
<220> FEATURE:
<223> OTHER INFORMATION: artificial polypeptide

<400> SEQUENCE: 13

Asn Ser Leu Ala Leu Ser Leu Thr Ala Asp Gln Met Val Ser Ala Leu
1               5                   10                  15

Leu Asp Ala Glu Pro Pro Ile Leu Tyr Ser Glu Tyr Asp Pro Thr Ser
            20                  25                  30

Pro Phe Ser Glu Ala Ser Met Met Gly Leu Leu Thr Asn Leu Ala Asp
        35                  40                  45

Arg Glu Leu Val His Met Ile Asn Trp Ala Lys Arg Val Pro Gly Phe
    50                  55                  60

Val Asp Leu Thr Leu His Asp Gln Ala His Leu Leu Glu Cys Ala Trp
```

```
            65                  70                  75                  80
Leu Glu Ile Leu Met Ile Gly Leu Val Trp Arg Ser Met Glu His Pro
                    85                  90                  95
Gly Lys Leu Leu Phe Ala Pro Asn Leu Leu Asp Arg Asn Gln Gly
                100                 105                 110
Lys Cys Val Glu Gly Met Val Glu Ile Phe Asp Met Leu Ala Thr
                115                 120                 125
Ser Ser Arg Phe Arg Met Met Asn Leu Gln Gly Glu Glu Phe Val Cys
            130                 135                 140
Leu Lys Ser Ile Ile Leu Leu Asn Ser Gly Val Tyr Thr Phe Leu Ser
145                 150                 155                 160
Ser Thr Leu Lys Ser Leu Glu Glu Lys Asp His Ile His Arg Ala Leu
                165                 170                 175
Asp Lys Ile Thr Asp Thr Leu Ile His Leu Met Ala Lys Ala Gly Leu
                180                 185                 190
Thr Leu Gln Gln Gln His Gln Arg Leu Ala Gln Leu Leu Ile Leu
                195                 200                 205
Ser His Ile Arg His Met Ser Asn Lys Gly Met Glu His Leu Tyr Ser
            210                 215                 220
Met Lys Tyr Thr Asn Val Val Pro Leu Tyr Asp Leu Leu Leu Glu Met
225                 230                 235                 240
Leu Asp Ala His Arg Leu His Ala
                245

<210> SEQ ID NO 14
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 14
tatgtacagg aacgcactat atctttcaaa gatgacggga actacgcatg c        51

<210> SEQ ID NO 15
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 15
gtgcacgaca accccttcgg cgacgagggt gtgcagttcc tcgacctcga g        51

<210> SEQ ID NO 16
<211> LENGTH: 45
<212> TYPE: DNA
<213> ORGANISM: Artificial Sequence
<220> FEATURE:
<223> OTHER INFORMATION: artificial polynucleotide

<400> SEQUENCE: 16
ctcgtttagt gaaccgtcag agccgccatg gcaagcaaag gagaa             45

<210> SEQ ID NO 17
<211> LENGTH: 45
<212> TYPE: DNA
<213> ORGANISM: Artificial Sequence
<220> FEATURE:
<223> OTHER INFORMATION: artificial polynucleotide
```

<400> SEQUENCE: 17
ctacttgtca tcgtcgtcct tgtaatcttt gtagagctca tccat        45

<210> SEQ ID NO 18
<211> LENGTH: 45
<212> TYPE: DNA
<213> ORGANISM: Artificial Sequence
<220> FEATURE:
<223> OTHER INFORMATION: artificial polynucleotide

<400> SEQUENCE: 18
acacatggca tggatgagct ctacaaagat tacaaggacg acgat        45

<210> SEQ ID NO 19
<211> LENGTH: 44
<212> TYPE: DNA
<213> ORGANISM: Artificial Sequence
<220> FEATURE:
<223> OTHER INFORMATION: artificial polynucleotide

<400> SEQUENCE: 19
ttcttctcct tgcttgcca tggcggctct gacggttcac taaa        44

<210> SEQ ID NO 20
<211> LENGTH: 45
<212> TYPE: DNA
<213> ORGANISM: Artificial Sequence
<220> FEATURE:
<223> OTHER INFORMATION: artificial polynucleotide

<400> SEQUENCE: 20
ttcgaggacg gcggcgtggt gaccgtgtgc cttgccgagg gtacc        45

<210> SEQ ID NO 21
<211> LENGTH: 45
<212> TYPE: DNA
<213> ORGANISM: Artificial Sequence
<220> FEATURE:
<223> OTHER INFORMATION: artificial polynucleotide

<400> SEQUENCE: 21
gccgtcctgc agggaggagt cctggcagtt gtgcacgaca acccc        45

<210> SEQ ID NO 22
<211> LENGTH: 45
<212> TYPE: DNA
<213> ORGANISM: Artificial Sequence
<220> FEATURE:
<223> OTHER INFORMATION: artificial polynucleotide

<400> SEQUENCE: 22
atccacgggg agcggaagga attcgtgtgc cttgccgagg gtacc        45

<210> SEQ ID NO 23
<211> LENGTH: 45
<212> TYPE: DNA
<213> ORGANISM: Artificial Sequence
<220> FEATURE:
<223> OTHER INFORMATION: artificial polynucleotide

<400> SEQUENCE: 23
ctccctcgag caacctcccc aatggcagtt gtgcacgaca acccc        45

<210> SEQ ID NO 24
<211> LENGTH: 45

```
<212> TYPE: DNA
<213> ORGANISM: Artificial Sequence
<220> FEATURE:
<223> OTHER INFORMATION: artificial polynucleotide

<400> SEQUENCE: 24
attcatggag aaaagaagga attcgtgtgc cttgccgagg gtacc              45

<210> SEQ ID NO 25
<211> LENGTH: 45
<212> TYPE: DNA
<213> ORGANISM: Artificial Sequence
<220> FEATURE:
<223> OTHER INFORMATION: artificial polynucleotide

<400> SEQUENCE: 25
ctctcgagaa caatcaagcc agcggcagtt gtgcacgaca acccc              45

<210> SEQ ID NO 26
<211> LENGTH: 21
<212> TYPE: DNA
<213> ORGANISM: Artificial Sequence
<220> FEATURE:
<223> OTHER INFORMATION: artificial polynucleotide

<400> SEQUENCE: 26
ctcgtcgccg aagggggttgt c                                        21

<210> SEQ ID NO 27
<211> LENGTH: 21
<212> TYPE: DNA
<213> ORGANISM: Artificial Sequence
<220> FEATURE:
<223> OTHER INFORMATION: artificial polynucleotide

<400> SEQUENCE: 27
atcgaagatt cgggtaccct c                                         21

<210> SEQ ID NO 28
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 28
cgcaagccta ttcatgtcgt ggctgttgcc aaggacggaa cgctgctcgc g        51

<210> SEQ ID NO 29
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 29
cgcgagcagc gttccgtcct tggcaacagc cacgacatga ataggcttgc g        51

<210> SEQ ID NO 30
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 30
```

```
gggttgcgga tcgccggtgg cgccatcgtg tgggcgacac ccgatcacaa g        51

<210> SEQ ID NO 31
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 31
cttgtgatcg ggtgtcgccc acacgatggc gccaccggcg atccgcaacc c        51

<210> SEQ ID NO 32
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 32
ttgttggatg ctgagccccc catactctat tccgagtatg atcctaccag t        51

<210> SEQ ID NO 33
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 33
actggtagga tcatactcgg aatagagtat gggggggctca gcatccaaca a        51

<210> SEQ ID NO 34
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 34
ccatgatcag gcccaccttc tagaacgtgc ctggctagag atcctgatga t        51

<210> SEQ ID NO 35
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 35
atcatcagga tctctagcca ggcacgttct agaaggtggg cctgatcatg g        51

<210> SEQ ID NO 36
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 36
gagcatctgt acagcatgaa gtacacgaac gtggtgcccc tctatgacct g        51

<210> SEQ ID NO 37
<211> LENGTH: 51
<212> TYPE: DNA
<213> ORGANISM: Artificial Sequence
```

```
<220> FEATURE:
<223> OTHER INFORMATION: artificial polynucleotide

<400> SEQUENCE: 37
caggtcatag aggggcacca cgttcgtgta cttcatgctg tacagatgct c        51

<210> SEQ ID NO 38
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 38
ttcctgcacg acatgctggc ggaagaactc cgctattccg tgatccgaga a        51

<210> SEQ ID NO 39
<211> LENGTH: 51
<212> TYPE: DNA
<213> ORGANISM: Artificial Sequence
<220> FEATURE:
<223> OTHER INFORMATION: artificial polynucleotide

<400> SEQUENCE: 39
ttctcggatc acggaatagc ggagttcttc cgccagcatg tcgtgcagga a        51
```

What is claimed is:

1. A ligand-dependent intein comprising an amino acid as provided in SEQ ID NO: 2 wherein the intein comprises at least one mutation selected from the group consisting of V34A, I66T, E375G, L124P, D129N, C178R, and T328K, and wherein the ligand-dependent intein does not comprise the amino acid sequence provided in SEQ ID NO: 1.

2. The intein of claim 1, wherein the intein comprises the amino acid sequence of intein 30R3-1:

(SEQ ID NO: 3)
CLAEGTRIFDPVTGTTHRIEDVVDGRKPIHVVA<u>A</u>AKDGTLLARPVVSWFDQGTRDVIGLRI

AGGAVWATPDHKVLTEYGWRAAGELRKGDRVAGPGGSGNSLALSLTADQMVSALLDA

EPPIYSEYDPTSPFSEASMMGLLTNLADRELVHMINWAKRVPGFVDLTLHDQAHLLECA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKY<u>K</u>NVVPLYDLLLEMLDAHRLHAGGSGASRVQAFAD

ALDDKFLHDMLAELRYSVIREVLPTRRARTFDLEVEELHTLVAEGVVVHNC;
or the amino acid sequence of intein 30R3-2:
(SEQ ID NO: 4)
CLAEGTRIFDPVTGTTHRIEDVVDGRKPIHVVAAAKDGTLLARPVVSWFDQGTRDVIGLRI

AGGATVWATPDHKVLTEYGWRAAGELRKGDRVAGPGGSGNSLALSLTADQMVSALLDA

EPPILYSEYDPTSPFSEASMMGLLTNLADRELVHMINWAKRVPGFVDLTLHDQAHLLECA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEELRYSVIREVLPTRRARTFDLEVEELHTLVAEGVVVHNC;
or the amino acid sequence of intein 30R3-3:
(SEQ ID NO: 5)
CLAEGTRIFDPVTGTTHRIEDVVDGRKPIHVVAAAKDGTLLARPVVSWFDQGTRDVIGLRI

AGGATVWATPDHKVLTEYGWRAAGELRKGDRVAGPGGSGNSLALSLTADQMVSALLDA

-continued

```
EPPIPYSEYDPTSPFSEASMMGLLTNLADRELVHMINWAKRVPGFVDLTLHDQAHLLECA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEELRYSVIREVLPTRRARTFDLEVEELHTLVAEGVVVHNC;
or the amino acid sequence of intein 37R3-1:
                                                   (SEQ ID NO: 6)
CLAEGTRIFDPVTGTTHRIEDVVDGRKPIHVVAAAKDGTLLARPVVSWFDQGTRDVIGLRI

AGGATVWATPDHKVLTEYGWRAAGELRKGDRVAGPGGSGNSLALSLTADQMVSALLDA

EPPILYSEYNPTSPFSEASMMGLLTNLADRELVHMINWAKRVPGFVDLTLHDQAHLLERA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEGLRYSVIREVLPTRRARTFDLEVEELHTLVAEGVVVHNC;
or the amino acid sequence of intein 37R3-2:
                                                   (SEQ ID NO: 7)
CLAEGTRIFDPVTGTTHRIEDVVDGRKPIHVVAAAKDGTLLARPVVSWFDQGTRDVIGLRI

AGGATVWATPDHKVLTEYGWRAAGELRKGDRVAGPGGSGNSLALSLTADQMVSALLDA

EPPILYSEYDPTSPFSEASMMGLLTNLADRELVHMINWAKRVPGFVDLTLHDQAHLLERA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEELRYSVIREVLPTRRARTFDLEVEELHTLVAEGVVVHNC;
or the amino acid sequence of intein 37R3-3:
                                                   (SEQ ID NO: 8)
CLAEGTRIFDPVTGTTHRIEDVVDGRKPIHVVAVAKDGTLLARPVVSWFDQGTRDVIGLRI

AGGATVWATPDHKVLTEYGWRAAGELRKGDRVAGPGGSGNSLALSLTADQMVSALLDA

EPPILYSEYDPTSPFSEASMMGLLTNLADRELVHMINWAKRVPGFVDLTLHDQAHLLERA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEELRYSVIREVLPTRRARTFDLEVEELHTLVAEGVVVHNC.
```

3. A protein comprising an N-terminal intein domain comprising the sequence

```
                                                   (SEQ ID NO: 10)
CLAEGTRIFDPVTGTTHRIEDVVDGRKPIHVVAV*AKDGTLLARPVVSWF

DQGTRDVIGLRIAGGAI*VWATPDHKVLTEYGWRAAGELRKGDRVA;
``` and a C-terminal intein domain comprising the sequence

```
                                                   (SEQ ID NO: 11)
RVQAFADALDDKFLHDMLAEE*LRYSVIREVLPTRRARTFDLEVEELHTL

VAEGVVVHN;
``` wherein the protein comprises at least one mutation selected from the group consisting of I*T, or E*G.

4. The protein of claim 3, wherein the protein further comprises a central ligand-binding domain between the N-terminal intein domain and the C-terminal intein domain comprising an estrogen-binding domain.

5. The protein of claim 4, wherein the central ligand-binding domain comprises amino acid residues 304-551 of the human estrogen receptor.

6. The protein of claim 4, wherein the estrogen-binding domain comprises the sequence

```
                                             (SEQ ID NO: 12)
NSLALSLTADQMVSALLDAEPPILYSEYDPTSPFSEASMMGLLTNLADRE

LVHMINWAKRVPGFVDLTLHDQAHLLECAWLEILMIGLVWRSMEHPGKLL

FAPNLLLDRNQGKCVEGMVEIFDMLLATSSRFRMMNLQGEEFVCLKSIIL

LNSGVYTFLSSTLKSLEEKDHIHRALDKITDTLIHLMAKAGLTLQQQHQR

LAQLLLILSHIRHMSNKGMEHLYSMKYTNVVPLYDLLLEMLDAHRLHA.
```

7. The protein of claim 4, wherein the estrogen-binding domain comprises the amino acid sequence NSLALSLTADQMVSALLDAEPPIL*YSEYD*PTSPFSE ASMMGLLTNLADRELVHMINWAK RVPGFVDLTLHD QAHLLEC*AWLEILMIGLVWRSMEHPGKLLFAPNLL LDRNQGKCVEGM VEIFDMLLATSSRFRMMNLQ-GEEFVCLKSIILLNSGVYTFLSSTLK-SLEEKDHIHRALDKITD TLIHLMAKAGLTLQQQH QRLAQLLLILSHIRHMSNKGMEHLYSMKYT*NVVPL YDLLLEM LDAHRLHA (SEQ ID NO: 13), wherein at least one of the residues L*, D*, C*, or T* is mutated.

8. The protein of claim 4, wherein the estrogen-binding domain comprises at least one of the following mutations: L*P, D*N, C*R, or T*K.

9. The protein of claim 3, wherein the intein comprises the amino acid sequence of intein 30R3-1:

```
                                                                 (SEQ ID NO: 3)
CLAEGTRIFDPVTGTTHRIEDVVDGRKPIHVVAAAKDGTLLARPVVSWFDQGTRDVIGLRI

AGGATVWATPDHKVLTEYGWRAAGELRKGDRVAGPGGSGNSLALSLTADQMVSALLDA

EPPIPYSEYDPTSPFSEASMMGLLTNLADRELVHMINWAKRVPGFVDLTLHDQAHLLECA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEGLRYSVIREVLPTRRARTFDLEVEELHTLVAEGVVVHNC;
or the amino acid sequence of intein 30R3-2:
                                                                 (SEQ ID NO: 4)
CLAEGTRIFDPVTGTTHRIEDVVDGRKPIHVVAAAKDGTLLARPVVSWFDQGTRDVIGLRI

AGGATVWATPDHKVLTEYGWRAAGELRKGDRVAGPGGSGNSLALSLTADQMVSALLDA

EPPILYSEYDPTSPFSEASMMGLLTNLADRELVHMINWAKRVPGFVDLTLHDQAHLLECA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEELRYSVIREVLPTRRARTFDLEVEELHTLVAEGVVVHNC;
or the amino acid sequence of intein 30R3-3:
                                                                 (SEQ ID NO: 5)
CLAEGTRIFDPVTGTTHRIEDVVDGRKPIHVVAAAKDGTLLARPVVSWFDQGTRDVIGLRI

AGGATVWATPDHKVLTEYGWRAAGELRKGDRVAGPGGSGNSLALSLTADQMVSALLDA

EPPIPYSEYDPTSPFSEASMMGLLTNLADRELVHMINWAKRVPGFVDLTLHDQAHLLECA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEELRYSVIREVLPTRRARTFDLEVEELHTLVAEGVVVHNC;
or the amino acid sequence of intein 37R3-1:
                                                                 (SEQ ID NO: 6)
CLAEGTRIFDPVTGTTHRIEDVVDGRKPIHVVAAAKDGTLLARPVVSWFDQGTRDVIGLRI

AGGATVWATPDHKVLTEYGWRAAGELRKGDRVAGPGGSGNSLALSLTADQMVSALLDA

EPPILYSEYNPTSPFSEASMMGLLTNLADRELVHMINWAKRVPGFVDLTLHDQAHLLERA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEGLRYSVIREVLPTRRARTFDLEVEELHTLVAEGVVVHNC;
``` or the amino acid sequence of intein 37R3-2:

(SEQ ID NO: 7)
CLAEGTRIFDPVTGTTHRIEDVVDGRKPIHVVAAAKDGTLLARPVVSWFDQGTRDVIGLRI

AGGATVWATPDHKVLTEYGWRAAGELRKGDRVAGPGGSGNSLALSLTADQMVSALLDA

EPPILYSEYDPTSPFSEASMMGLLTNLADRELVHMINWAKRVPGFVDLTLHDQAHLLERA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEELRYSVIREVLPTRRARTFDLEVEELHTLVAEGVVVHNC;
or the amino acid sequence of intein 37R3-3:

(SEQ ID NO: 8)
CLAEGTRIFDPVTGTTHRIEDVVDGRKPIHVVAVAKDGTLLARPVVSWFDQGTRDVIGLRI

AGGATVWATPDHKVLTEYGWRAAGELRKGDRVAGPGGSGNSLALSLTADQMVSALLDA

EPPILYSEYDPTSPFSEASMMGLLTNLADRELVHMINWAKRVPGFVDLTLHDQAHLLERA

WLEILMIGLVWRSMEHPGKLLFAPNLLLDRNQGKCVEGMVEIFDMLLATSSRFRMMNLQG

EEFVCLKSIILLNSGVYTFLSSTLKSLEEKDHIHRALDKITDTLIHLMAKAGLTLQQQHQRLA

QLLLILSHIRHMSNKGMEHLYSMKYKNVVPLYDLLLEMLDAHRLHAGGSGASRVQAFAD

ALDDKFLHDMLAEELRYSVIREVLPTRRARTFDLEVEELHTLVAEGVVVHNC.

10. A method of using a ligand-dependent intein, the method comprising
   (a) contacting a target cell with a hybrid protein comprising the ligand-dependent intein of claim 1 inserted into the amino acid sequence of a target protein, or with a polynucleotide encoding such a hybrid protein; and
   (b) contacting the cell with tamoxifen or a tamoxifen analog in an amount that effects self-excision of the ligand-dependent intein from the hybrid protein in at least about 10% of the hybrid protein molecules.

11. The protein of claim 3, wherein amino acid residue V* is substituted with A.

12. The protein of claim 3, wherein the protein is an intein.

* * * * *